(12) United States Patent
Albanawi et al.

(10) Patent No.: US 10,940,094 B2
(45) Date of Patent: Mar. 9, 2021

(54) PILL DISPENSING ASSEMBLY

(71) Applicant: Pilleve, Inc., Washington, DC (US)

(72) Inventors: Yossuf Albanawi, Washington, DC (US); Gautam Sai Chebrolu, Columbus, GA (US)

(73) Assignee: Pilleve, Inc., Washington, DC (US)

( * ) Notice: Subject to any disclaimer, the term of this patent is extended or adjusted under 35 U.S.C. 154(b) by 0 days.

(21) Appl. No.: 16/394,809

(22) Filed: Apr. 25, 2019

(65) Prior Publication Data

US 2019/0328616 A1   Oct. 31, 2019

Related U.S. Application Data

(60) Provisional application No. 62/663,756, filed on Apr. 27, 2018.

(51) Int. Cl.
*A61J 1/03* (2006.01)
*A61J 7/04* (2006.01)
(Continued)

(52) U.S. Cl.
CPC .......... *A61J 7/0427* (2015.05); *A61J 7/0076* (2013.01); *A61J 7/0445* (2015.05); *G16H 20/13* (2018.01);
(Continued)

(58) Field of Classification Search
None
See application file for complete search history.

(56) References Cited

U.S. PATENT DOCUMENTS 5,292,029 A    3/1994  Pearson
6,299,019 B1 * 10/2001 Leight .................. A61F 15/001
                                                   221/186
(Continued)

FOREIGN PATENT DOCUMENTS

WO   2007/071818 A1   6/2007
WO   2013/127564 A1   9/2013
WO   2018/035147 A1   2/2018

OTHER PUBLICATIONS

"A Smart Pill Box Uses Face Recognition Tech to Ensure we Take our Meds", retrieved on Jul. 9, 2020 from https://www.popsci.com/science/article/2011-01/smart-pill-box-taps-face-recognition-tech-ensure-we-take-our-meds/.
(Continued)

*Primary Examiner* — Gene O Crawford
*Assistant Examiner* — Ayodeji T Ojofeitimi
(74) *Attorney, Agent, or Firm* — Fiala & Weaver P.L.L.C.

(57) ABSTRACT

A pill dispensing assembly comprises a pill bottle that is securely locked between a base and an attachable sleeve. The pill bottle and base form an enclosure in which pills are stored above a top portion of a dosing mechanism of the base. The top portion of the dosing mechanism comprises a ramp and a rotating arm that carries a pill from a base of the ramp to a position in which the pill will drop through an aperture in a bottom portion of the dosing mechanism into a channel that connects the aperture to a dispensing slot in a housing of the base. The base includes a microcontroller that interacts with a servomotor to control rotation of the arm and thereby the dispensing of a pill. The base also includes a wireless communication interface that enables the dispensing of the pill to be controlled by a remote entity.

20 Claims, 20 Drawing Sheets

(51) Int. Cl.
*A61J 7/00* (2006.01)
*G16H 20/13* (2018.01)
*B65D 83/04* (2006.01)

(52) U.S. Cl.
CPC ............... *A61J 1/03* (2013.01); *A61J 7/0481* (2013.01); *A61J 2200/70* (2013.01); *B65D 83/0481* (2013.01)

(56) References Cited

U.S. PATENT DOCUMENTS

| | | | |
|---|---|---|---|
| 6,380,858 | B1 | 4/2002 | Yarin et al. |
| 7,269,476 | B2 | 9/2007 | Ratnakar |
| 7,359,765 | B2 | 4/2008 | Varvarelis et al. |
| 7,537,005 | B2 | 5/2009 | Dave |
| 7,715,277 | B2 | 5/2010 | De La Huerga |
| 7,877,268 | B2 | 1/2011 | Kulkarni |
| 8,212,677 | B2 | 7/2012 | Ferguson |
| 9,199,772 | B2 | 12/2015 | Krippendorf |
| 9,251,314 | B2 | 2/2016 | Kanagala |
| 9,358,183 | B2 | 6/2016 | Stein et al. |
| 9,373,239 | B2 | 6/2016 | Ebe |
| 9,730,860 | B2 | 8/2017 | Hamilton |
| 2007/0016443 | A1 | 1/2007 | Wachman et al. |
| 2008/0173666 | A1* | 7/2008 | Coe ................... B65D 83/0409 221/265 |
| 2008/0303638 | A1 | 12/2008 | Nguyen et al. |
| 2011/0060457 | A1 | 3/2011 | De Vrught et al. |
| 2012/0313785 | A1 | 12/2012 | Hanson et al. |
| 2014/0074283 | A1 | 3/2014 | Blackburn |
| 2014/0263390 | A1* | 9/2014 | Seneff ..................... G07F 11/04 221/7 |
| 2014/0278510 | A1 | 9/2014 | McLean et al. |
| 2014/0288942 | A1* | 9/2014 | Blochet ..................... A61J 7/04 705/2 |
| 2014/0305963 | A1 | 10/2014 | Zonana et al. |
| 2014/0326636 | A1 | 11/2014 | Baschnagel |
| 2015/0343144 | A1 | 12/2015 | Altschul et al. |
| 2016/0042150 | A1 | 2/2016 | Moloughney |
| 2016/0096675 | A1* | 4/2016 | Dai ........................ A61F 11/08 221/277 |
| 2016/0120758 | A1 | 5/2016 | Pi et al. |
| 2016/0287480 | A1 | 10/2016 | Hancock et al. |
| 2016/0357940 | A1 | 12/2016 | Carter et al. |
| 2016/0374902 | A1 | 12/2016 | Govindasamy et al. |
| 2017/0000692 | A1 | 1/2017 | Mullen |
| 2017/0281471 | A1 | 10/2017 | Hamilton |
| 2018/0039756 | A1 | 2/2018 | Phipps et al. |
| 2019/0328619 | A1 | 10/2019 | Albanawi et al. |

OTHER PUBLICATIONS

"Apps Aim to Prevent Overdoses, Support Recovering Users," retrieved on Jul. 9, 2020 from https://www.rochesterfirst.com/news/local-news/apps-aim-to-prevent-overdoses-support-recoveringusers/.

"Pill Drill," retrieved from https://www.pilldrill.com on Jul. 9, 2020.

Comstock, Jonah "Slideshow: 8 Pillboxes that Connect to Your Phone", Mar. 13, 2013, retrieved from https://www.mobihealthnews.com/20795/slideshow-8-pillboxes-that-connect-to-your-phone on Jul. 9, 2020.

Intent Solutions, "A Smart Moble Medication Dispenser", 2017, retrieved from http://intentsolutions.com/ on Jul. 9, 2020.

Jeffries, "Smart Pill Bottle Measures Meds Using Touchscreen Technology", Oct. 8, 2012, retrieved from the https://www.theverge.com/2012/10/08/3473218/smart-pill-bottle-adheretech-capacitance on Jul. 9, 2020.

Lumma, "Lumma, Smart Pill Dispenser", Mar. 9, 2015, retrieved from https://www.kickstarter.com/projects/402921688/lumma-automated-medication-sorter-and-dispenser on Jun. 23, 2020.

Salgia et al., "Smart Pill Box", Indian Journal of Science and Technology; vol. 8(S2), Jan. 2015, pp. 189-194.

Tricella, "Tricella Liif 7 Green Smart Pillbox with Family Notifications", retrieved from https://www.amazon.com./Tricella-Liif-Green-Smart-Pillbox/dp/B019ML021U on Jun. 24, 2020.

* cited by examiner

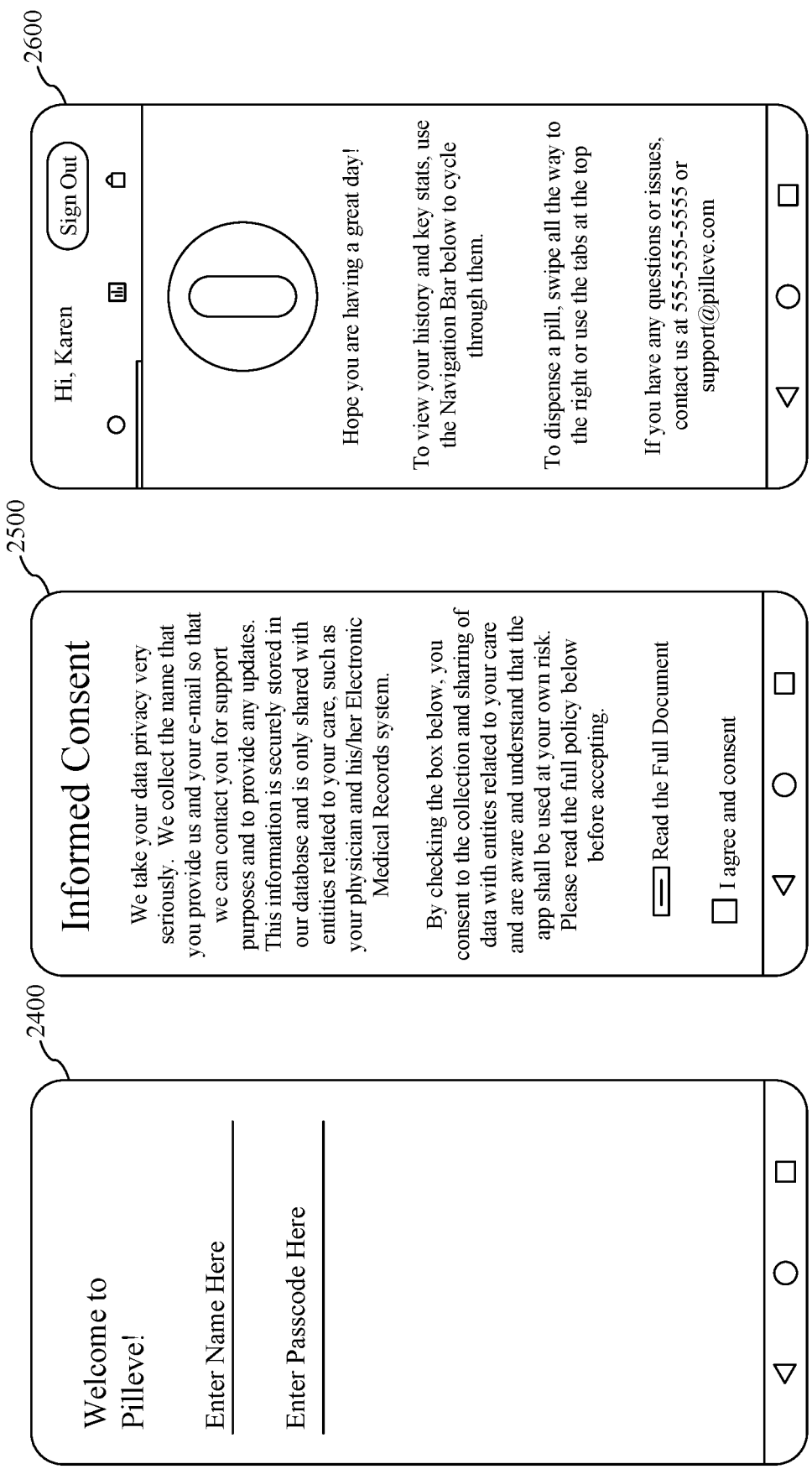

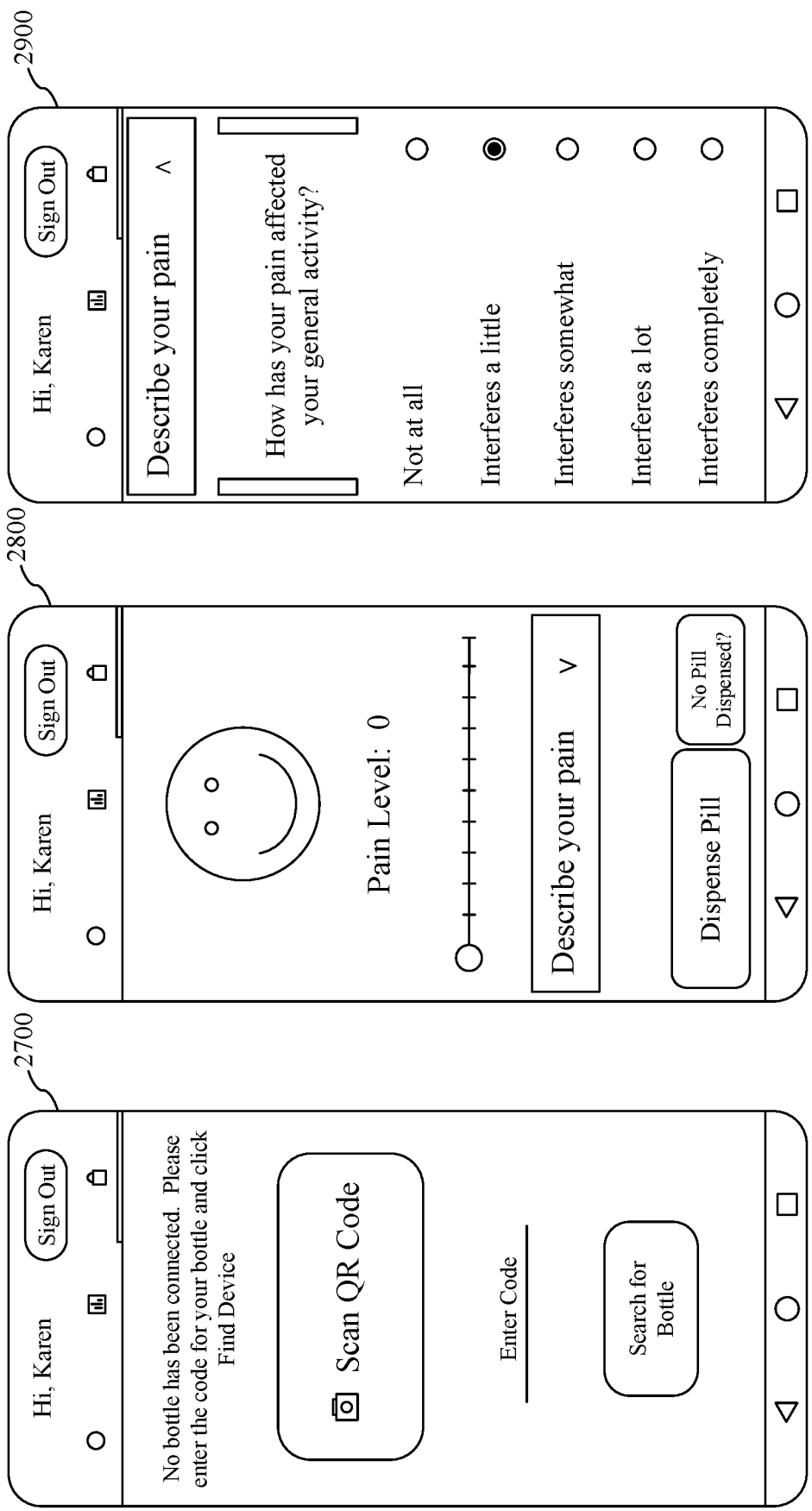

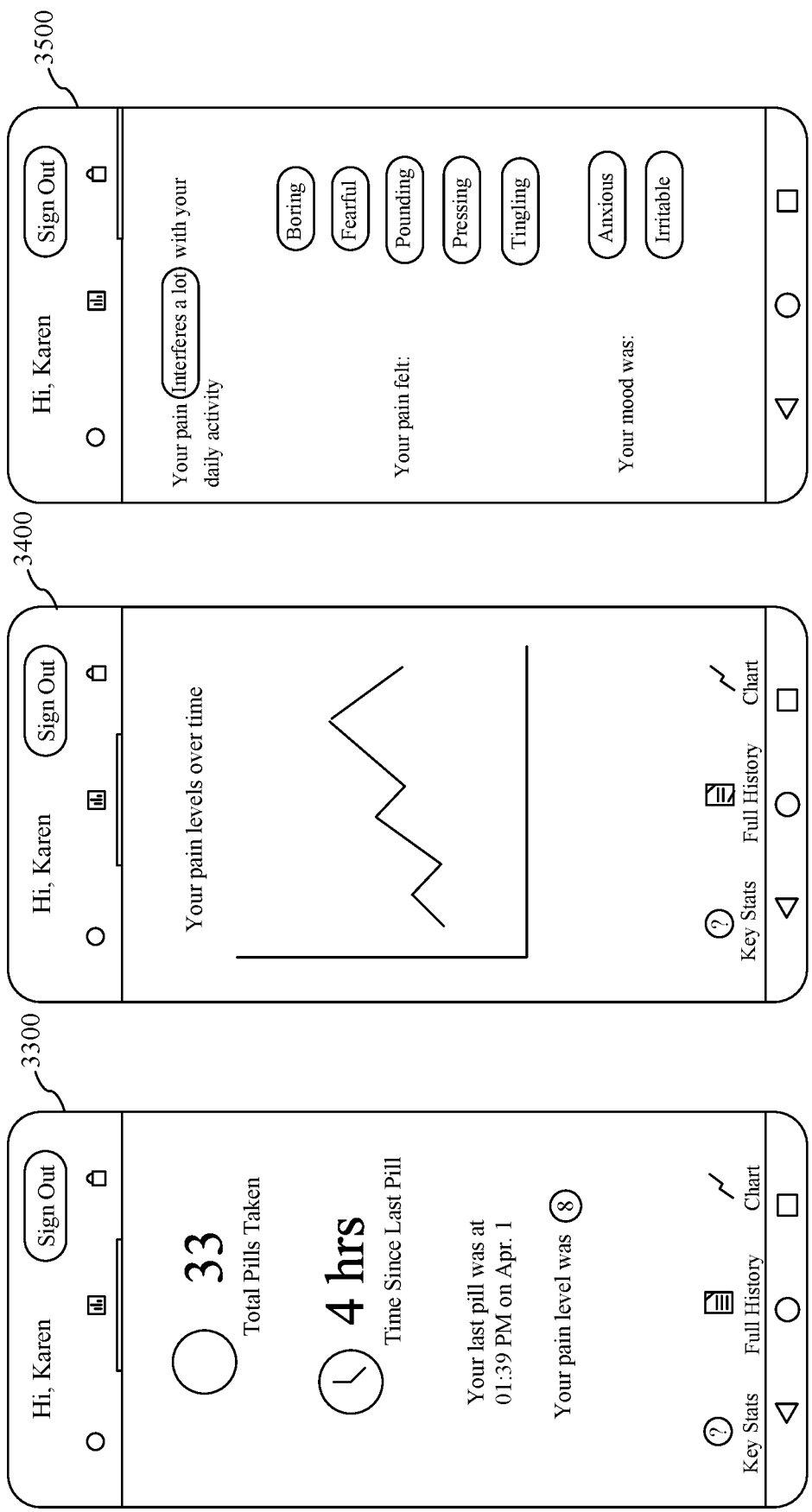

PILL DISPENSING ASSEMBLY

CROSS-REFERENCE TO RELATED APPLICATIONS

This application claims priority to U.S. Provisional Patent Application No. 62/663,756, entitled "Apparatus and Method to Deliver Virtual Healthcare for Pain Management" and filed on Apr. 27, 2018, the entirety of which is incorporated by reference herein.

BACKGROUND

To date, the opioid epidemic is the largest public health crises in the history of the United States, leaving millions of Americans addicted and killing tens of thousands of people a year. Overprescription has been one of the main drivers of this epidemic. Throughout the last two decades, pharmaceutical companies have advocated for the treatment of chronic and acute pain with painkillers, specifically opioids such as Oxycontin® and Percocet®. This led to a massive increase in prescriptions, with annual prescriptions of opioids in the U.S. easily exceeding two hundred million a year. Unfortunately, patient safety tools and guidelines didn't catch up as addiction began increasing amongst the population.

Federal, state, and local governments began implementing a few solutions to combat this growing crisis, such as Prescription Drug Monitoring Programs (PDMPs), that have proven to reduce overdoses. However, providers and payers are still in need of preventive tools that work remotely and target patients at the 'point of intake', which is where most abuse and misuse occurs. Further, the need for timely and complete data, as outlined by the Center of Medicare and Medicaid, has never been more important. Data at the point of intake has the ability to bridge the gap between prescription and addiction because it accounts for the behaviors that often lead to addiction, such as increased intake, while shedding light on how a patient engages with their medication at any point in time. Further, the relationship between a patient and their prescription is remote in nature, making it difficult to screen for aberrant behaviors just by relying on monthly check ups at the clinics.

Physicians are only confined to a few minutes every month to screen for signs of aberrant behaviors, limiting their scope and ability to intervene. Moreover, insurance companies are not able to respond to a patient who develops a costly addiction except by carrying the brunt of the cost or offsetting it by skyrocketing premiums. Loved ones are finding out years too late and can sometimes be the facilitators of addiction by leaving behind leftover opioids in unsecure bottles and locations.

The opioid crisis is a national health crisis that takes tens of thousands of lives every year, resulting in millions of Americans suffering from an opioid abuse disorder. Aside from the social costs, healthcare payers are spending over $25 billion to treat every year. Further, prescribers are at risk due to the increased scrutiny and some are losing their practices due to overprescription. This leaves patients who may need opioid therapy without proper treatment, increasing their risk of misusing unprescribed drugs.

BRIEF SUMMARY

A pill dispensing assembly is described herein. The pill dispensing assembly comprises a pill bottle that is securely locked between a base and an attachable sleeve. The pill bottle and base form an enclosure in which pills are stored above a top portion of a dosing mechanism of the base. The top portion of the dosing mechanism comprises a ramp and a rotating arm that carries a pill from a base of the ramp to a position in which the pill will drop through an aperture in a bottom portion of the dosing mechanism into a channel that connects the aperture to a dispensing slot in a housing of the base. The base includes a microcontroller that interacts with a servomotor to control rotation of the arm and thereby the dispensing of a pill. The base also includes a wireless communication interface that enables the dispensing of the pill to be controlled by a remote entity.

A pill dispensing system is also described herein. The pill dispensing assembly comprises a pill dispensing assembly and an application executing on a device. The pill dispensing assembly includes an enclosure that stores one or more pills, a dosing mechanism, a wireless communication interface, and a microcontroller that is connected to the dosing mechanism and the wireless communication interface, the microcontroller being configured to activate the dosing mechanism to dispense a pill from the enclosure in response to the receipt of a control signal via the wireless communication interface. The application is configured to send the control signal to the microcontroller via the wireless communication interface in response to an interaction therewith by a user. Pill dispensing event data may be collected by the application and stored in a remote backend database and uploaded at a user's discretion to a physician and/or pharmacists electronic health record (EHR)/EMR system.

BRIEF DESCRIPTION OF THE DRAWINGS/FIGURES

The accompanying drawings, which are incorporated herein and form a part of the specification, illustrate the present methods and systems and, together with the description, further serve to explain the principles of the methods and systems and to enable a person skilled in the pertinent art to make and use the methods and systems.

FIGS. 22-35 show example graphical user interface screens of the application of FIG. 21.

Figure 1:
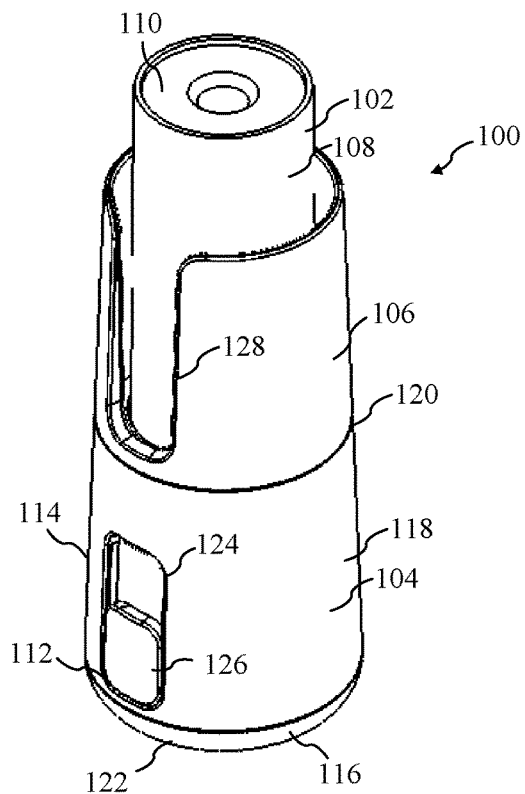
FIG. 1 shows a perspective view of a pill dispensing assembly in accordance with an embodiment.
Figure 2:
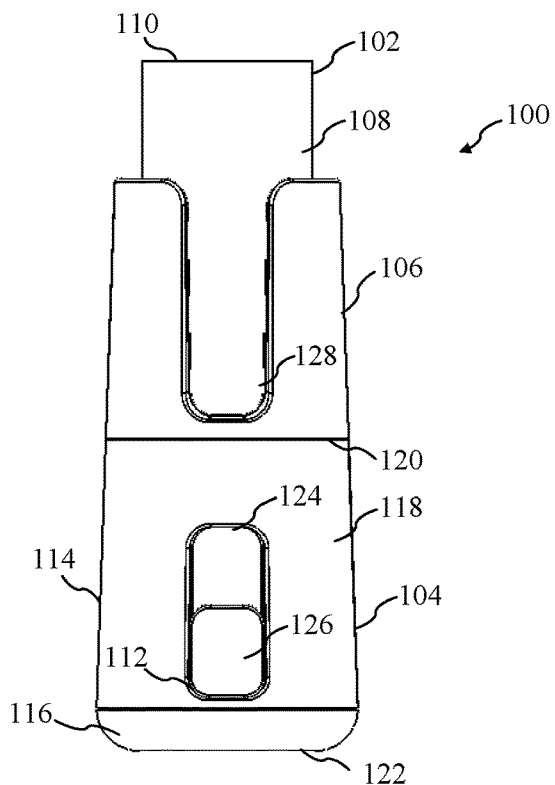
FIG. 2 shows a front view of the pill dispensing assembly of FIG. 1.
Figure 3:
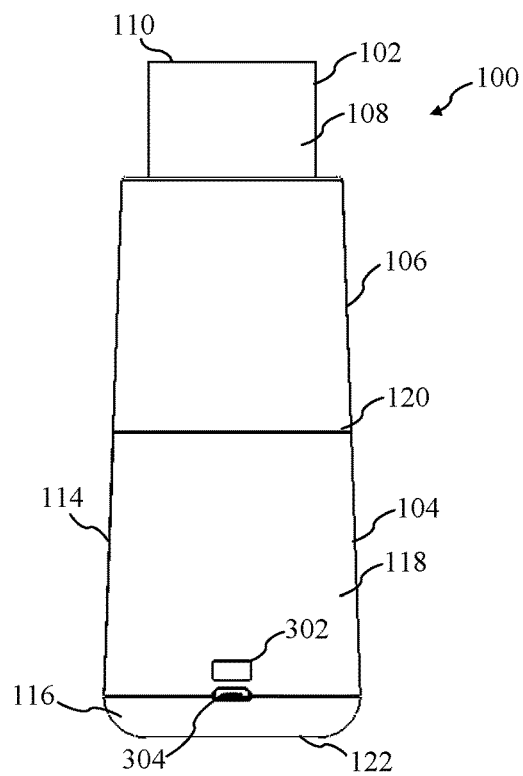
FIG. 3 shows a back view of the pill dispensing assembly of FIG. 1.
Figure 4:
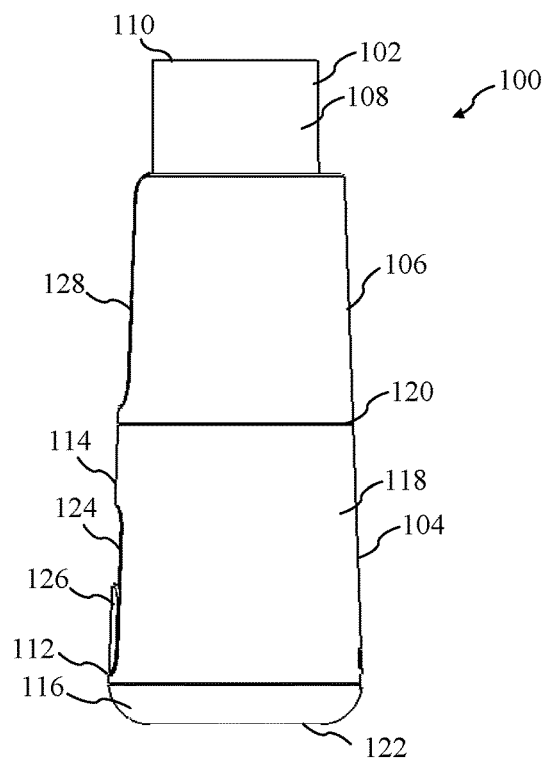
FIG. 4 shows a side view of the pill dispensing assembly of FIG. 1.
Figure 5:
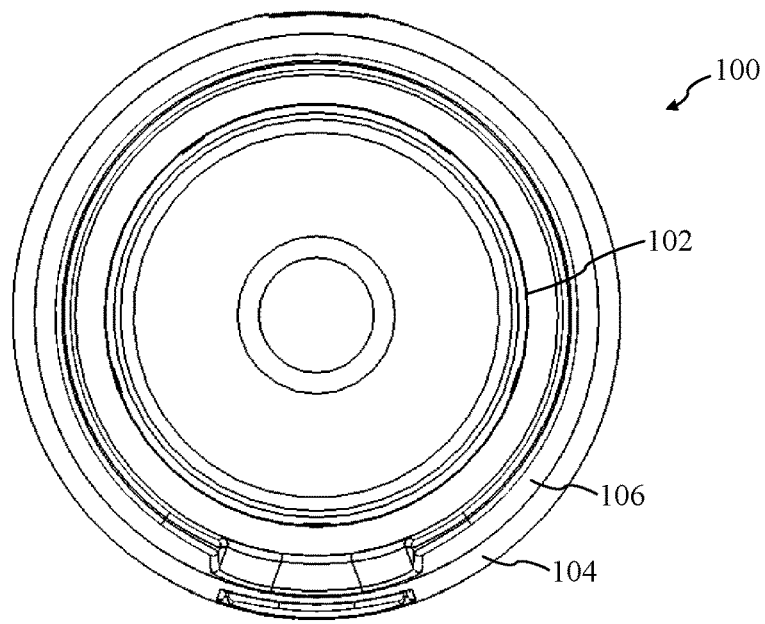
FIG. 5 shows a top view of the pill dispensing assembly of FIG. 1.

The features and advantages of the embodiments described herein will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

I. Introduction

The present specification and accompanying drawings disclose one or more embodiments that incorporate the features of the present invention. The scope of the present invention is not limited to the disclosed embodiments. The disclosed embodiments merely exemplify the present invention, and modified versions of the disclosed embodiments are also encompassed by the present invention. Embodiments of the present invention are defined by the claims appended hereto.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which it is intended.

Furthermore, it should be understood that spatial descriptions (e.g., "above," "below," "up," "left," "right," "down," "top," "bottom," "vertical," "horizontal," etc.) used herein are for purposes of illustration only, and that practical implementations of the structures described herein can be spatially arranged in any orientation or manner.

Still further, it should be noted that the drawings/figures are not drawn to scale unless otherwise noted herein.

Numerous exemplary embodiments are described as follows. It is noted that any section/subsection headings provided herein are not intended to be limiting. Embodiments are described throughout this document, and any type of embodiment may be included under any section/subsection. Furthermore, embodiments disclosed in any section/subsection may be combined with any other embodiments described in the same section/subsection and/or a different section/subsection in any manner.

A pill dispensing assembly is described herein. In embodiments, the pill dispensing assembly comprises a pill bottle that is securely locked between a base and an attachable sleeve. The pill bottle and base form an enclosure in which pills are stored above a top portion of a dosing mechanism of the base. The top portion of the dosing mechanism comprises a ramp and a rotating arm that carries a pill from a base of the ramp to a position in which the pill will drop through an aperture in a bottom portion of the dosing mechanism into a channel that connects the aperture to a dispensing slot in a housing of the base. The base includes a microcontroller that interacts with a servomotor to control rotation of the arm and thereby the dispensing of a pill. The base also includes a wireless communication interface that enables the dispensing of the pill to be controlled by a remote entity.

A pill dispensing system is also described herein. In embodiments, the pill dispensing assembly comprises a pill dispensing assembly and an application executing on a device. The pill dispensing assembly includes an enclosure that stores one or more pills, a dosing mechanism, a wireless communication interface, and a microcontroller that is connected to the dosing mechanism and the wireless communication interface, the microcontroller being configured to activate the dosing mechanism to dispense a pill from the enclosure in response to the receipt of a control signal via the wireless communication interface. The application is configured to send the control signal to the microcontroller via the wireless communication interface in response to an interaction therewith by a user. Pill dispensing event data may be collected by the application and stored in a remote backend database and uploaded at a user's discretion to a physician and/or pharmacists electronic health record (EHR)/EMR system.

The pill dispensing assembly and system described herein can provide many advantages and benefits including ensuring that patients use their prescription drugs (e.g., opioids) properly and safely, which also has the effect of lowering the risk to prescribers and reducing costs to payers. For example, the pill dispensing assembly described herein places controls around the pill dispensing process that will discourage misuse of the pills stored therein. Furthermore, the pill dispensing assembly in combination with the application provide a means for continuously monitoring usage of pain medication by a patient, where in the information collected can benefit the patient and optionally the patient's physician so that compliance with a prescription may be ensured and scenarios that lead to addiction or abuse can be avoided.

II. Example Embodiments

A. Example Pill Dispensing Assembly

FIGS. 1-15 depict an example pill dispensing assembly 100 as well as various components thereof in accordance with an embodiment. As shown in these figures, pill dispensing assembly 100 comprises several interconnected components including a pill bottle 102, a base 104, and a sleeve 106. Generally speaking, pill bottle 102 is used to store pills that have yet to be dispensed to a user, base 104 provides a mechanism for dispensing such pills from pill bottle 102 to a user of pill dispensing assembly 100 and also performs other functions relating to remote control and monitoring of the pill dispensing function, while sleeve 106 provides a surface upon which a prescription label may be affixed. Base 104 and sleeve 106 also include mating components that enable these components to be securely locked to each other which has the effect of also securely locking pill bottle 102 there between.

In one example usage scenario envisioned for pill dispensing assembly 100, a pharmacist may fill pill bottle 102 with a number of pills as part of filling a patient's prescription. The pharmacist may then take base 104 (shown in perspective view in FIG. 8), invert it, and slide an open end of base 104 over an open end of pill bottle 102. Then, through a twisting motion, the pharmacist may lock base 104 onto pill bottle 102, in a like manner to how a pill bottle cap is twisted onto a pill bottle. The pharmacist may then turn the connected base 104 and pill bottle 102 over so that the bottom of pill bottle 102 is facing upward (e.g., as in the configuration shown in FIG. 10). In this position, the pharmacist may then slide sleeve 106 (shown in perspective view in FIG. 12) down over the bottom of pill bottle 102 so that a mating end of sleeve 106 locks into the top of base 104, thereby also locking pill bottle 102 there between and completing pill bottle assembly 100. At this point, the pharmacist may apply prescription labelling to an external face of sleeve 106 and provide pill bottle assembly 100 to the patient.

To continue with this example usage scenario, when the patient subsequently wishes to dispense a pill from pill dispensing assembly 100, the patient interacts with an application executing on a mobile device (e.g., a smartphone) that has been communicatively linked (e.g., through a BLUETOOTH® pairing process) to a microcontroller housed within base 104. Responsive to such interaction, the application causes a signal to be sent from the mobile device to the microcontroller that causes the microcontroller to activate a pill dispensing mechanism within base 104. Such pill dispensing mechanism, when activated, will cause a single pill to drop from inside of pill bottle 102 into a dispensing slot 112 of base 104, where it can be obtained by the patient. The aforementioned locking of base 104 to pill bottle 102 and the subsequent locking of sleeve 106 to base 104 causes pill bottle 102 to be securely captured between the other two components in a manner that makes accessing the pills stored therein (outside of the aforementioned dispensing mechanism of base 104) extremely difficult.

These and numerous other features and benefits of pill bottle assembly 100 will now be further described with continued reference to FIGS. 1-15.

As shown in the relevant figures, pill bottle 102 comprises a cylindrical body 108 and a circular bottom 110 that together define a pill bottle cavity 1102. A top end 1104 of cylindrical body 108 defines a circular opening 1106 that is opposite to circular bottom 110. A pharmacist may fill a prescription by depositing one or more pills within pill bottle cavity 1102 via circular opening 1106. This action may preferably be performed with circular opening 1106 facing upward to prevent the pills from falling out of pill bottle 102. In embodiments, pill bottle 102 may advantageously comprise a plastic pill bottle commonly used by pharmacies to fill prescriptions, such as a conventional plastic 6-dram, 8-dram, or 13-dram pill bottle. However, these examples are not intended to be limiting and any type of pill bottle composed of any type of material may be used to implement pill dispensing assembly 100. Pill bottle 102 may be transparent or semi-transparent such that any pills stored therein may be visible to a user of pill dispensing assembly 100 (e.g., a pharmacist or patient).

An external radial ridge 1108 at top end 1104 of pill bottle 102 comprises five regularly-spaced female snap fit elements that extend outward therefrom. Three of these female snap fit elements (namely, female snap fit elements 1502a, 1502b and 1502c, respectively) can be best observed in the exploded view of FIG. 15, while the remaining elements cannot be seen but should be understood to be included within the design. Each of these female snap fit elements is generally bayonet-shaped. In one embodiment, these female snap fit elements comprise standard pill bottle elements designed to engage with corresponding male snap fit elements of a conventional pill bottle cap. However, this need not be the case and nonconventional mating elements may be used as well.

Base 104 comprises a housing 114 that includes a bottom portion 116, a top portion 120, and a middle portion 118 that connects bottom portion 116 to top portion 120. Bottom portion 116 of housing 114 comprises a relatively wide and substantially flat base 122 that advantageously facilitates stable placement of pill bottle assembly 100 on a variety of surfaces without tipping. It is also noted that various electronic components, including a printed circuit board and rechargeable battery, are disposed within housing 114 of base 104, thereby rendering pill dispensing assembly 100 "bottom heavy", and thus inherently more stable.

Middle portion 118 of housing 114 is generally shaped like a tapered cylinder. Middle portion 118 of housing 114 comprises a substantially rectangular-shaped recess 124 that accommodates a substantially square-shaped sliding door 126. By applying an upward pressure to sliding door 126, a user can move sliding door 126 upward within recess 124 to access a pill in the aforementioned pill dispensing slot 112, which is accessible via a bottom portion of recess 124. For example, side walls of recess 124 may comprise grooves within which portions of sliding door 126 may slide, thereby allowing for upward and downward movement of sliding door 126. In an embodiment, sliding door 126 is spring-biased to return to the downward position shown in FIG. 1 when no pressure is being applied to it by a user. In this downward position, sliding door 112 substantially covers pill dispensing slot 112 which is otherwise accessible via the bottom portion of recess 124. This has the beneficial effect of maintaining a more air-tight environment for the pills currently stored in pill dispensing assembly 100, which can help prevent pills stored therein from being degraded through contact with the air (e.g., through contact with humid air). This also has the beneficial effect of ensuring that a dispensed pill is not ejected onto the floor after the user has activated the dispensing mechanism.

Middle portion 118 of housing 114 also defines apertures via which a multi-purpose button 302 and a charging port 304 can be respectively accessed. As will be discussed in more detail herein, multi-purpose button 302 may be actuated to perform functions such as waking a microprocessor within pill dispensing assembly 100 from a sleep state or causing the microprocessor to establish a wireless communication link with a mobile device such as a smart phone (e.g., through BLUETOOTH® pairing). The function that is performed in response to actuation of multi-purpose button 302 may vary, for example, based on how long multi-purpose button 302 is pressed or on how many times multi-purpose button 302 is pressed. Multi-purpose button 302 may also include an integrated light emitting diode (LED) that can be used to convey information to a user of pill dispensing assembly 100. For example, patterns of light (e.g., steady, blinking, slow blinking, fast blinking, or other patterns) and/or colors of light (in an embodiment in which the LED comprises a multi-color LED) can be used to convey various items of information to the user. Charging port 304 may be configured to accept a charging cable connector (e.g., a micro USB connector) so that a rechargeable battery within base 104 of pill dispensing assembly 100 can be recharged. As will be discussed in further detail herein, such rechargeable battery may be used to provide power to the various electronic components within base 104.

Figure 8:
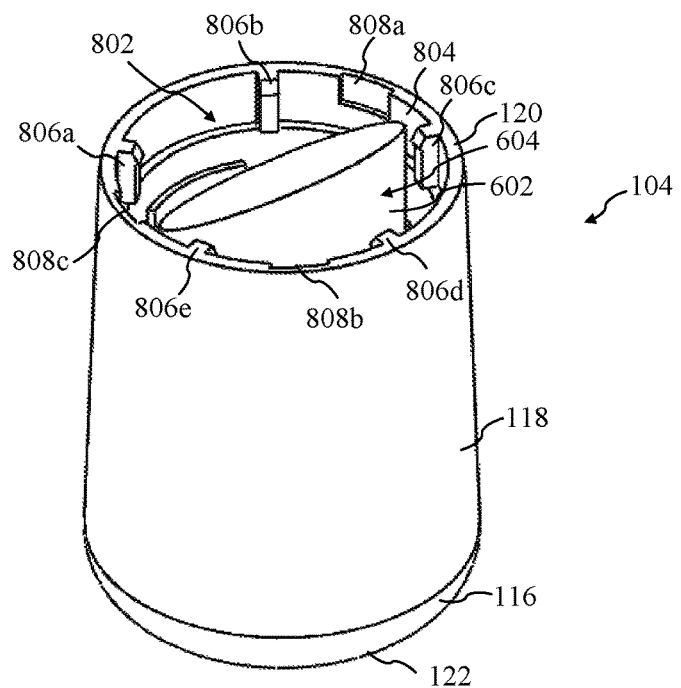
FIG. 8 shows a perspective view of a base of the pill dispensing assembly of FIG. 1.
Figure 9:
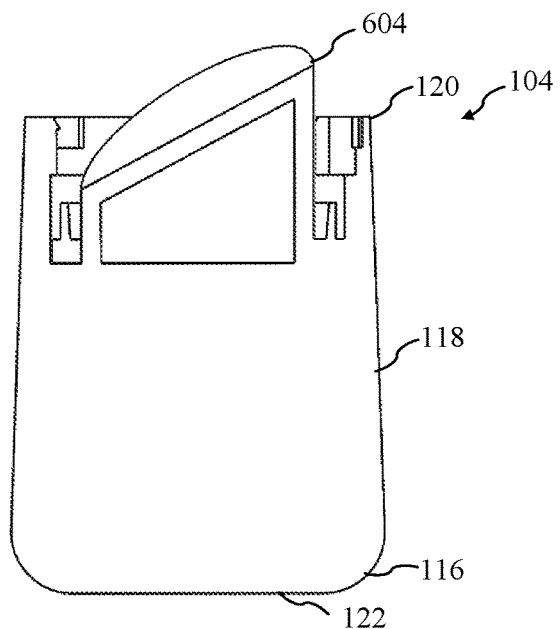
FIG. 9 shows a cross-sectional side view of the base of the pill dispensing assembly of FIG. 1.

As can be seen in FIG. 8, top portion 120 of housing 114 of base 104 comprises a circular recess 802 within which is disposed a ramp-shaped top portion 604 of a dosing mechanism 602, the structure and operation of which will be described below. Circular recess 802 comprises an internal edge 804 that surrounds ramp-shaped top portion 604 of dosing mechanism 602. Internal edge 804 comprises five rib-shaped male snap fit elements 806a, 806b, 806c, 806d, and 806e that extend therefrom and three female mating elements 808a, 808b and 808c that are inset therein.

As discussed above, a pharmacist may manually connect base 104 to pill bottle 102. This may be achieved by first aligning male snap fit elements 806a-806e on internal edge 804 of circular recess 802 of base 104 with five corresponding gaps between the female snap fit elements on external radial ridge 1108 at top end 1104 of pill bottle 102 and then sliding circular recess 802 of base 104 over top end 1104 of pill bottle 102. Without such alignment, the female snap fit elements on external radial ridge 1108 will block male snap fit elements 806a-806e and prevent the sliding of circular recess 802 of base 104 over top end 1104 of pill bottle 102.

Figure 10:
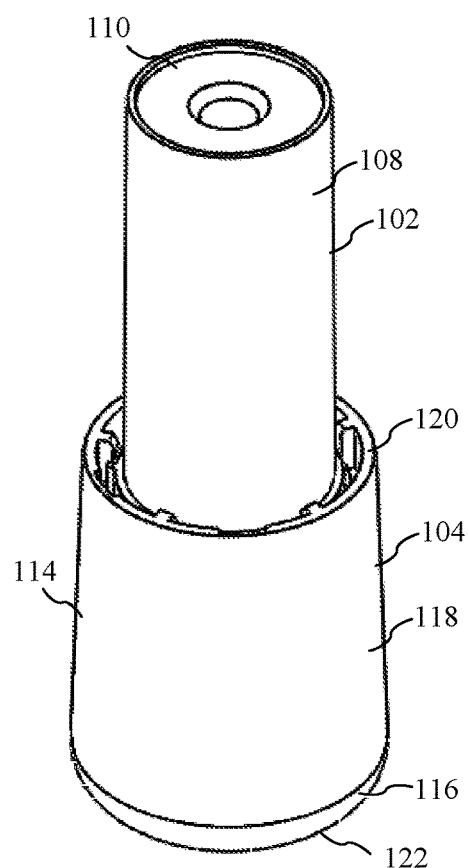
FIG. 10 shows a perspective view of a pill bottle and the base of the pill dispensing assembly of FIG. 1 in which the pill bottle is locked to the base.
Figure 11:
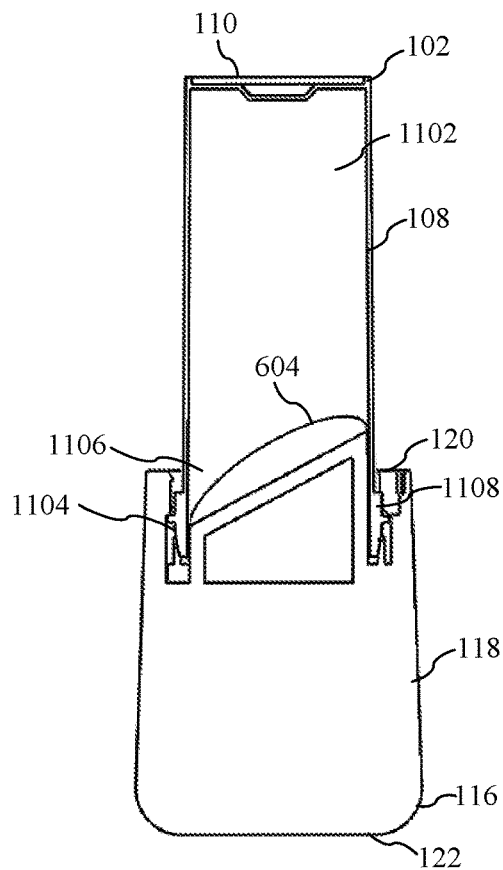
FIG. 11 shows a cross-sectional side view of the pill bottle and base of the pill dispensing assembly of FIG. 1 in which the pill bottle is locked to the base.

After circular recess 802 of base 104 has been slid over top end 1104 of pill bottle 102, the pharmacist may then turn base 104 (and/or turn pill bottle 102) so that male snap fit elements 806a-806e of base 104 lock into corresponding female snap fit elements on external radial ridge 1180 of pill bottle 102. As a result of the twisting action, the rib-shaped male snap fit elements 806a-806e will slide along a ramp-shaped portion of the bayonet-shaped female snap fit elements and then lock into place into slots/grooves formed by such bayonet-shaped female snap fit elements. FIG. 10 shows a perspective view in which pill bottle 102 has been locked into base 104 in accordance with this technique, while FIG. 11 shows a cross-sectional view of the same components in which the engagement between a rib-shaped male snap fit element of base 104 and a bayonet-shaped female snap fit element of pill bottle 102 can be observed.

Figure 12:
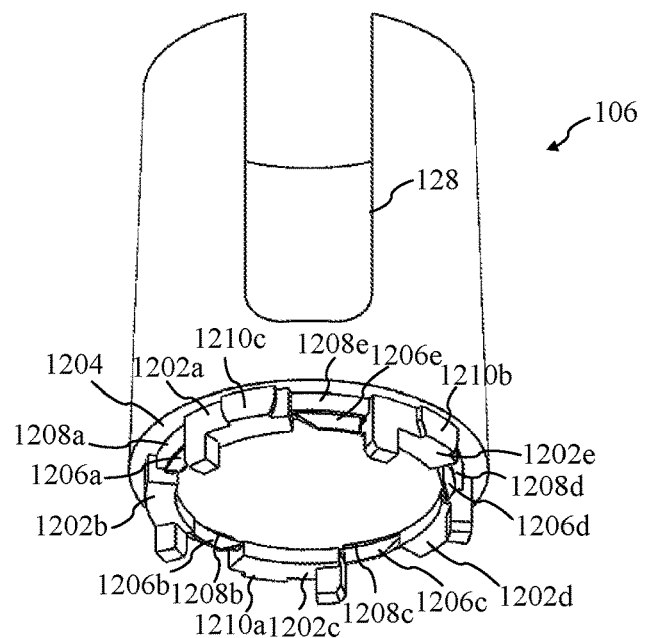
FIG. 12 shows a perspective view of a sleeve of the pill dispensing assembly of FIG. 1.

Sleeve 106 comprises a structure that is generally shaped like a hollow tapered cylinder and defines an elongated gap 128 that is substantially rectangular in shape. Sleeve 106 also comprises a number of mating elements that are configured to enable sleeve 106 to be locked to base 104 in a manner that captures pill bottle 102 securely there between. In particular, and as can be seen in FIG. 12, sleeve 106 comprises five mating elements 1202a, 1202b, 1202c, 1202d and 1202e that are regularly spaced around a circular bottom 1204 of sleeve 106. A respective connector 1206a, 1206b, 1206c, 1206d and 1206e connects each of the mating elements to each other and forms a corresponding gap 1208a, 1208b, 1208c, 1208d and 1208e between each connector and circular bottom 1204. Each of the five mating elements 1202a-1202e comprises a lug that extends downward and away from circular bottom 1204. Three of the five mating elements, namely mating elements 1202c, 1202e and 1202a, respectively comprise outward-facing male mating elements 1210a, 1210b and 1210c.

As was mentioned above, when base 104 and pill bottle 102 are connected in a manner such as that shown in FIG. 10, a pharmacist may slide sleeve 106 down over the bottom of pill bottle 102 so that a mating end of sleeve 106 locks into the top of base 104, thereby completing pill bottle assembly 100. To achieve this, the pharmacist must first align the three male mating elements 1210a-1210c of sleeve 106 with the three female mating elements 808a-808c of base 104, which also has the effect of aligning the five connectors 1206a-1206e of sleeve 106 with the corresponding rib-shaped male snap fit elements 806a-806e of base 104. In this alignment (and this alignment only), the five mating elements 1202a-1202e can be slid into a circular gap between base 104 and pill bottle 102. As a result of this process, a protruding knob or hook at the top of each of rib-shaped male snap fit elements 806a-806e of base 104 will hook into (i.e., engage with) a corresponding gap 1208a-1208e formed by connectors 1206a-1206e of sleeve 106, thereby locking sleeve 106 to base 104 and locking the bayonet-shaped female snap fit elements of pill bottle 102 there between. Furthermore, as a result of this process, the downward-facing lugs of mating element 1202a-1202e will be locked into place in between each of the bayonet-shaped female snap fit elements of pill bottle 102, thereby impeding rotation of pill bottle 102 relative to either base 104 or sleeve 106.

Figure 13:
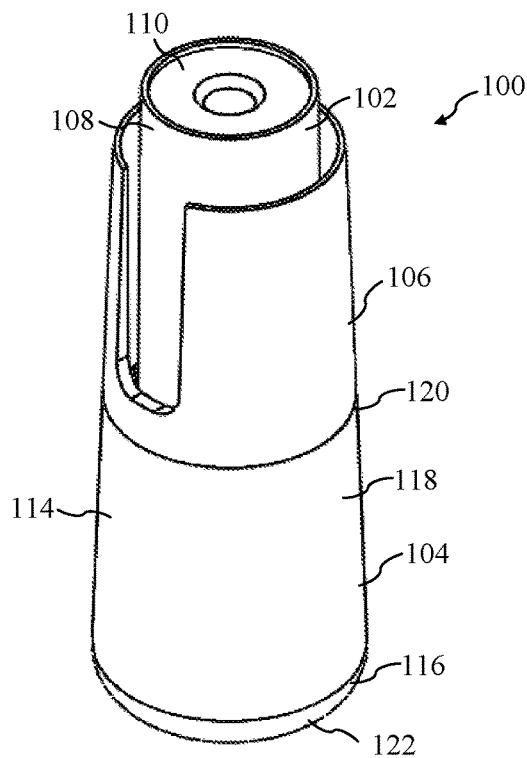
FIG. 13 shows a perspective view of the sleeve, pill bottle and base of the pill dispensing assembly of FIG. 1 in which both the pill bottle and the sleeve are locked to the base.
Figure 14:
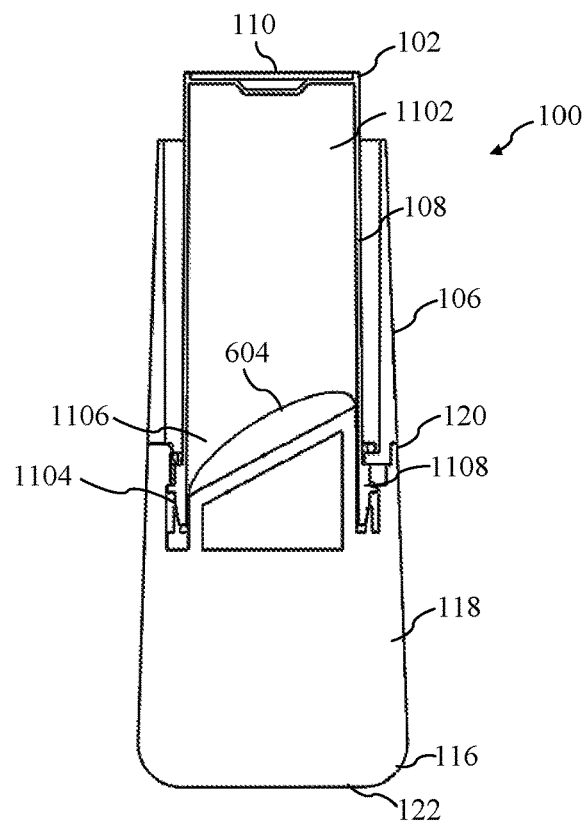
FIG. 14 shows a cross-sectional side view of the sleeve, pill bottle and base of the pill dispensing assembly of FIG. 1 in which both the pill bottle and the sleeve are locked to the base.
Figure 15:
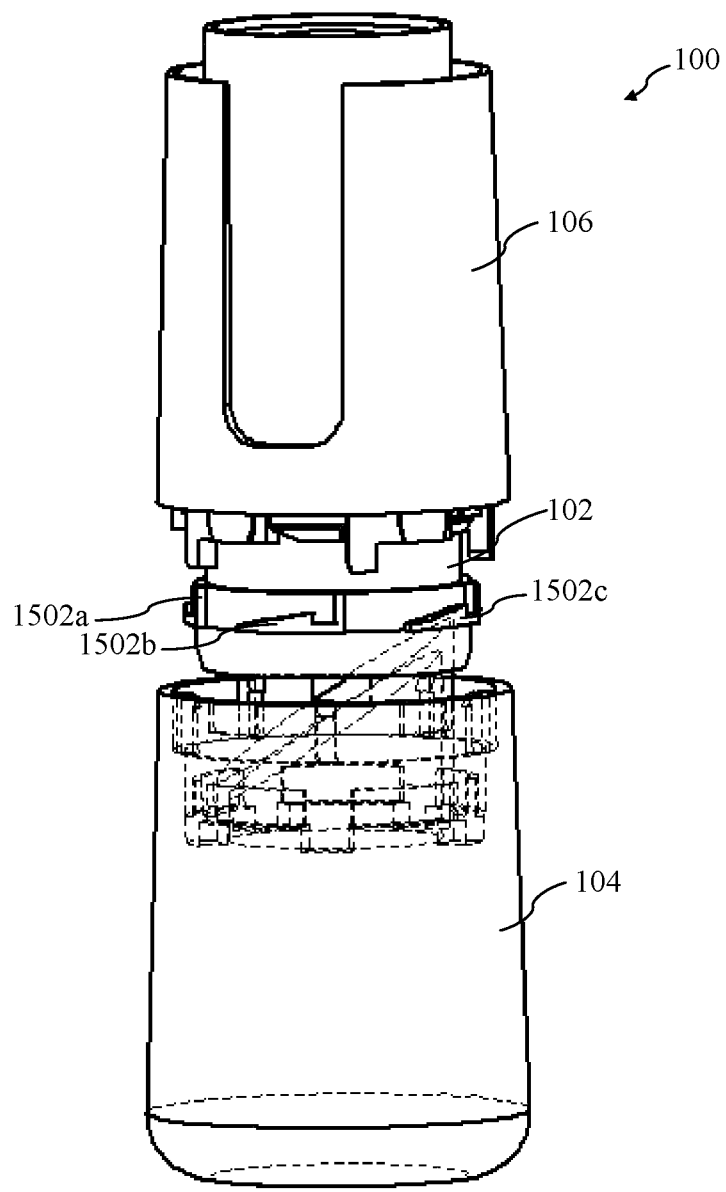
FIG. 15 shows an exploded view of the pill dispensing assembly of FIG. 1.

FIG. 13 shows a perspective view in which sleeve 106 has been locked into base 104 in accordance with this technique, thereby locking pill bottle 102 in between both components, while FIG. 14 shows a cross-sectional view of the same components in which the engagement between a male mating element of sleeve 106 and a female mating element of base 104 can be observed and in which the placement of a downward-facing lug of a sleeve 106 mating element between the bayonet-shaped female snap fit elements of pill bottle 102 can also be observed. By securely locking pill bottle 102 between base 104 and sleeve 106 in the manner described above, pill dispensing assembly 100 makes accessing the pills stored therein (outside of the aforementioned dispensing mechanism of base 104) extremely difficult.

In embodiments, sleeve 106 and housing 114 of base 104 are each made of plastic. For example, in embodiments, housing 114 of base 104 and sleeve 106 are each manufactured from polyethylene terephthalate (PET), a clear, strong, and lightweight plastic that is widely used for packaging foods and beverages. However, other plastics, including other food-grade plastics, may be used to implement these parts. Moreover, materials other than plastic could conceivably be used to implement these parts.

As was mentioned above, once sleeve 106 has been connected to base 104, a pharmacist may affix a prescription label to an external face thereof before providing pill bottle assembly 100 to a patient. In accordance with certain embodiments and usage scenarios, sleeve 106 may be considered a disposable component that can be removed and replaced by a pharmacist at a time of prescription refill or when it is desired to reuse pill bottle assembly to fill a new prescription. A new prescription label can then be affixed to the new replacement sleeve 106. Removing and replacing sleeve 106 at such times may be deemed a better alternative to placing a new prescription label over an old prescription label on sleeve 106. Likewise, removing and replacing sleeve 106 at such times may be deemed a better alternative to requiring a pharmacist to scrape off an old prescription label and then place a new prescription label over remains of a scraped-off label on sleeve 106.

Figure 16:
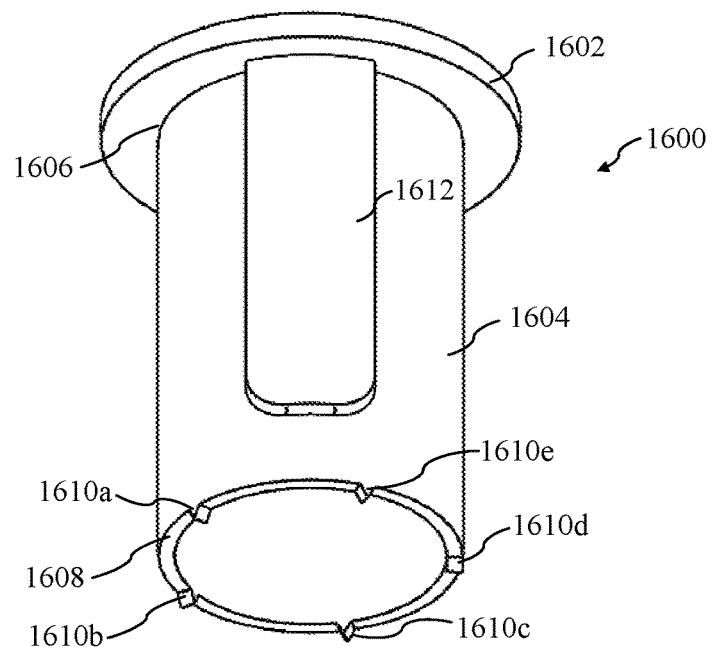
FIG. 16 shows a perspective view of a removal tool that may be used to remove the sleeve and pill bottle from the base of the pill dispensing assembly of FIG. 1.

In such embodiments/scenarios, the pharmacist will need to remove sleeve 106 and pill bottle 102 from base 104, despite the fact that these components are locked together. To assist the pharmacist in doing this, a special removal tool may be provided that enables the pharmacist to quickly and easily remove sleeve 106 and pill bottle 102 from base 104. FIG. 16 shows a perspective view of an example removal tool 1600 that may be used to perform this function. As shown in FIG. 16, removal tool 1600 comprises a circular disk 1602 and a cylindrical body 1604. Circular disk 1602 is connected to a first end 1606 of cylindrical body 1604. A second end 1608 of cylindrical body that is opposite to first end 1606 comprises five regularly-spaced spikes 1610a, 1610b, 1610c, 1610d and 1610e that extend downward therefrom. Cylindrical body 1604 comprises a guide element 1612 that projects therefrom and is substantially rectangular in shape.

Figure 17:
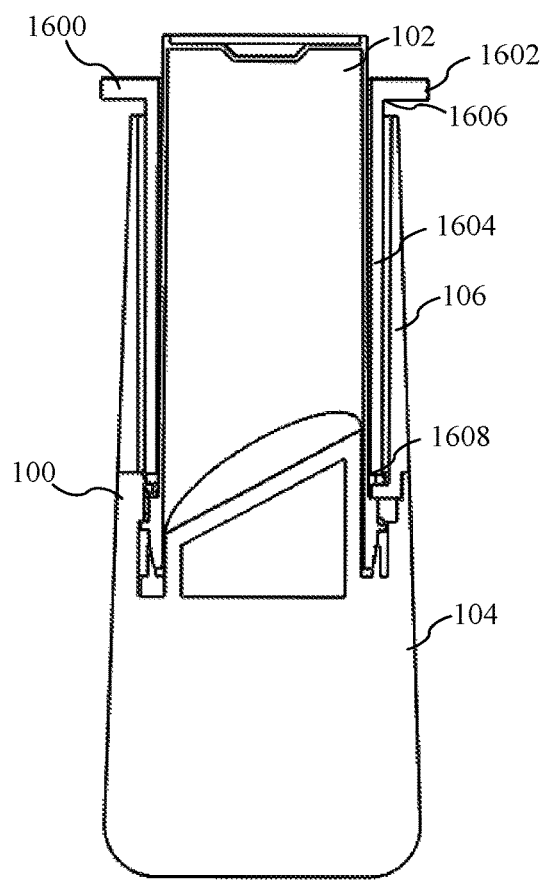
FIG. 17 shows a cross-sectional side view of the pill dispensing assembly of FIG. 1 and the removal tool of FIG. 15, wherein the removal tool is being applied to remove the sleeve and the pill bottle from the base of the pill dispensing assembly.

To utilize removal tool 1600, the pharmacist may place second end 1608 of removal tool 1600 over circular bottom 110 of pill bottle 102 and then apply pressure to circular disk 1602 (e.g., with her fingers) to push removal tool 1600 downward between sleeve 106 and pill bottle 102 and also between base 104 and pill bottle 102. The insertion of removal tool 1600 in this manner can be observed in the cross-sectional view of FIG. 17. Note that guide element 1612 must be aligned with gap 128 of sleeve 106 in order for this to be accomplished. This aspect of the design ensures that spikes 1610a, 1610b, 1610c, 1610d and 1610e are positioned such that they will come into contact with connectors 1206a, 1206b, 1206c, 1206d and 1206e of sleeve 106, respectively, and with sufficient pressure will break such connectors. The breaking of connectors 1206a-1206e enables sleeve 106 to be removed from body 104. Once sleeve 106 is removed from body 104, pill bottle 102 can be removed from body 104 by simply pressing and turning pill bottle 102 (and/or body 104) to disengage the male snap fit elements of body 104 from the female snap fit elements of pill bottle 102.

As can be seen in FIG. 12, connectors 1206a-1206e are advantageously shaped in such a manner that they will break with sufficient pressure from spikes 1610a-1610e but will still remain connected to sleeve 106 as opposed to breaking off and falling into base 104 or elsewhere. In particular, as shown in FIG. 12, each connector comprises relatively thin connection points by which it is joined to its adjacent mating elements and furthermore has one tapered end. In accordance with the aforementioned design, a corresponding spike will break the thin connection point at the non-tapered end of each connector. The tapered end will then act as a hinge when the connector is broken, enabling the connector to fold away in a manner that allows it to remain attached to sleeve 106 after the connector is broken.

After pill dispensing assembly 100 has been assembled in the manner described above, a number of pills will be enclosed in pill bottle 102 atop top portion 604 of dosing mechanism 602. That is to say, the interior of pill bottle 102 and top portion 604 of dosing mechanism together will define an enclosure in which such pills are securely stored. In this configuration, outside of readily apparent tampering with and/or damage to pill dispensing assembly 100, the only way for pills to be dispensed from pill dispensing assembly 100 will be via the operation of dosing mechanism 602 which will now be described.

Figure 6:
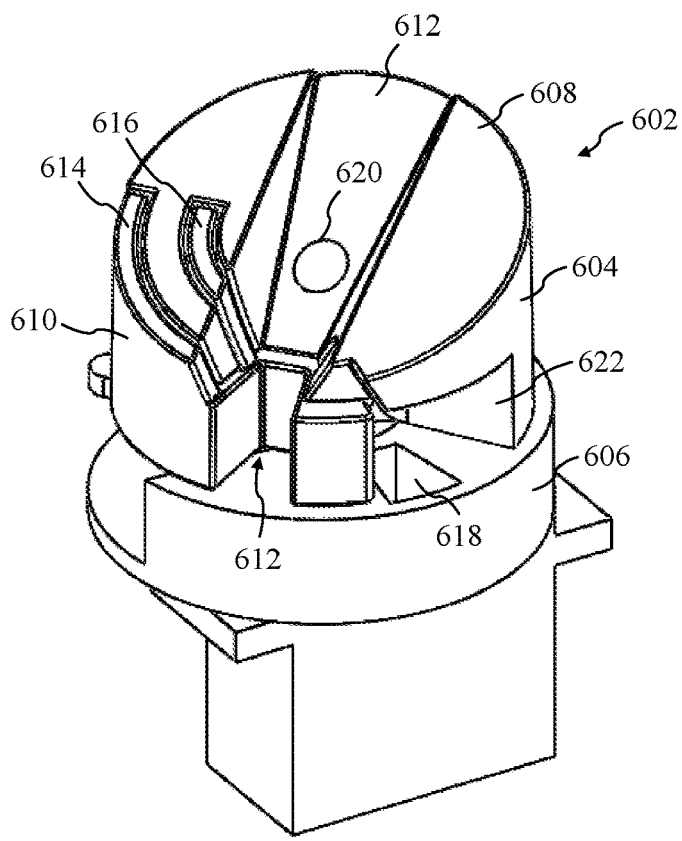
FIG. 6 shows a perspective view of a dosing mechanism of the pill dispensing assembly of FIG. 1 in which a rotating arm of the dosing mechanism is in a retracted state.

As shown in FIG. 6, dosing mechanism 602 comprises top portion 604 and a bottom portion 606 that is connected thereto. Top portion 604 of dosing mechanism 602 comprises a circular ramp 608 and a rotating arm 610 that is axially joined thereto. Circular ramp 608 includes a central chute 612 that has a relatively steeper incline than the remainder of circular ramp 608. Rotatable arm 610 defines a notch 612 and comprises two elevated ridges 614 and 616. Rotating arm 610 is rotatable by operation of a servomotor (not shown in FIG. 6) to rotate from a retracted state to an extended state and back to the retracted state.

When rotating arm 610 is in the retracted state (as shown in FIG. 6), elevated ridges 614 and 616 are inserted into corresponding grooves that are defined within circular ramp 608 and a side wall of central chute 612, thereby creating a substantially smooth or unbroken ramp/chute surface. In this retracted state, notch 612, an inner wall of pill bottle 102, and bottom portion 606 of dosing mechanism 602 together define a cavity into which a single pill may drop. For example, by virtue of gravity and the fact that both circular ramp 608 and central chute 612 are sloped towards the cavity, a single pill may slide therein from the enclosure defined by pill bottle 102 and top portion 604 of dosing mechanism 602. In an embodiment, notch 612 is sized and shaped in such a manner that only a single pill may be accommodated within the aforementioned cavity, thereby reducing or obviating a risk that more than one pill may be dispensed at a time.

Figure 7:
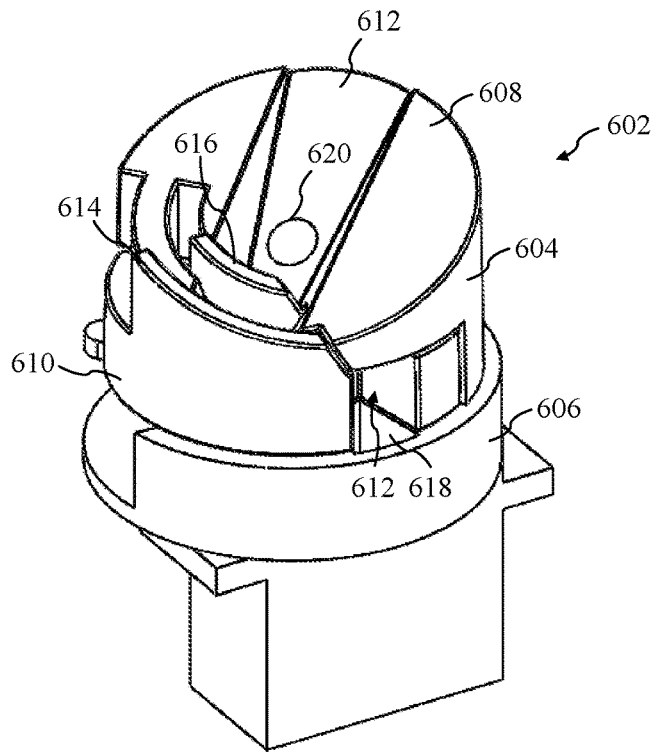
FIG. 7 shows a perspective view of the dosing mechanism of the pill dispensing assembly of FIG. 1 in which the rotating arm of the dosing mechanism is in an extended state.

When rotating arm 610 is rotated from the retracted state to the extended state (as shown in FIG. 7), notch 612 will be guided into position over an aperture 618 defined within bottom portion 606 of dosing mechanism 602. Aperture 618 is connected to an internal channel within base 104 (not shown) that comprises an arc-shaped ramp and a vertical chute that is in turn connected to dispensing slot 112. Thus, when rotating arm 610 is the retracted state shown in FIG. 6 and a pill has dropped into the aforementioned cavity defined by notch 612, internal wall of pill bottle 102, and middle portion 604 of dosing mechanism 602, and then rotating arm 610 is rotated to the extended state shown in FIG. 7, gravity will cause the pill will to drop through aperture 618, slide down the aforementioned arc-shaped ramp and then drop down the aforementioned vertical chute to be deposited into dispensing slot 112 where it may be retrieved by a user of pill dispensing assembly 100. Thus, the rotation of rotating arm 610 under operation of the servomotor will cause a single pill to be dispensed. After this pill dispensing process occurs, the servomotor may cause rotating arm 610 to return to its retracted state and the pill dispensing process can be carried out again so long as pills remain within the enclosure defined by pill bottle 102 and top portion 604 of dosing mechanism 602.

In an embodiment, due to the sloping shape of circular ramp 608 and central chute 612, two or more pills may be drawn into an area immediately above the cavity defined by notch 612, inner wall of pill bottle 102, and middle portion 604 of dosing mechanism 602 when rotating arm 610 is the retracted state shown in FIG. 6. These pills may conflict with or impede each other, thereby preventing any pill from dropping into the cavity and thus inhibiting the pill dispensing process. One way to address this issue is for a user of pill dispensing assembly 100 to shake pill dispensing assembly 100 until one or more of the mutually-blocked pills are propelled away from the relevant area and a single pill is allowed to pass into the cavity. However, to further address this issue, dosing mechanism 602 advantageously includes several design elements that will now be described.

In particular, as shown in FIGS. 6 and 7, central chute 612 may include a protuberance 620 that extends upward therefrom. Although protuberance 620 is shown as a circular placeholder in FIGS. 6 and 7, it is to be understood that such protuberance may comprise a structure having any of a variety of shapes (e.g., a hump, a cone, a dome, a cube, a cylinder, etc.) that extends from a bottom portion of central chute 612. By virtue of the placement of protuberance 620 within central chute 612, pills sliding down central chute 612 will tend to be propelled away from each other by protuberance 620 as they approach the aforementioned cavity. This disruption in the flow of pills down chute 612 will have the beneficial effect of reducing the chance that such pills will end up blocking each other in the area above the cavity.

The goal of disrupting pills clustered in the area above the cavity may also be addressed by virtue of the rotation of elevated ridges 614 and 616 of rotating arm 610. For example, as shown in FIG. 7, when rotating arm 610 is rotated to the extended state as part of the pill dispensing process, elevated ridges 614 and 616 thereof will be rotated directly into the area at the bottom of central chute 612, thereby disrupting any pills that may have accumulated there. This will also have the beneficial effect of reducing pill blocking in the area above the cavity. In an embodiment, the aforementioned servomotor may be controlled to rotate elevated ridges 614 and 616 into the bottom of central chute 612 one or more times in order to clear pills that may be clustered there. This rotation may not necessarily comprise a full rotation such as that used to dispense a pill but may also comprise one or more partial rotations for the purpose of disrupting a blockage.

In another embodiment, the aforementioned servomotor may be controlled to rotate rotating arm 610 so that it impacts a wall 622 of a cavity defined by top portion 604 of dosing mechanism 602 (see FIG. 6), which may create a vibration that will disrupt a blockage. Such rotation of rotating arm 610 into wall 622 may be carried out one or more times to try and disrupt the blockage.

Figure 18:
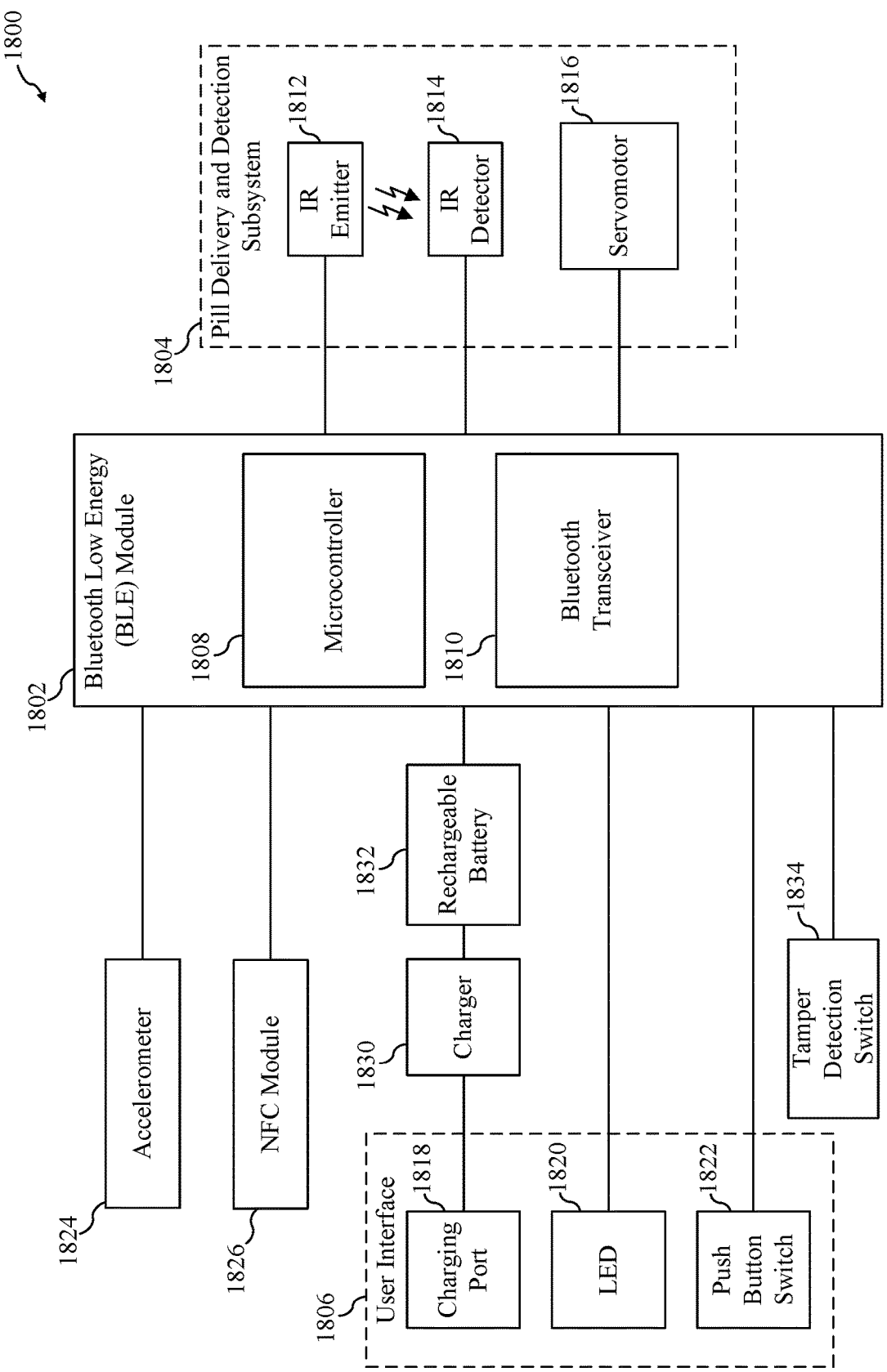
FIG. 18 is a block diagram of an electronic system that is contained within a base of the pill dispensing assembly of FIG. 1.

FIG. 18 is a block diagram of an electronic system 1800 that is contained within base 104 of pill dispensing assembly 100. One or more components of electronic system 1800 may be housed on a printed circuit board (PCB) that is disposed within an internal cavity of base 104 (e.g., an internal cavity defined by housing 114), while other components may be situated elsewhere within base 104 and/or externally exposed via an aperture in housing 114. Each of the components of electronic system 1800 will now be described.

As shown in FIG. 18, electronic system 1800 includes a Bluetooth low energy (BLE) module 1802 that comprises a microcontroller 1808 and a Bluetooth transceiver 1810. In one embodiment, BLE module 1802 comprises a RIGADO® Bluetooth BMD-300 Series BLE Module, which itself comprises a NORDIC® Semiconductor Bluetooth Low Energy System on Chip (SOC). In accordance with such an implementation, microcontroller 1808 comprises an ARM® Cortex™-M4 CPU. However, this is only one example implementation, and numerous other commercially-available and/or proprietary devices or circuits may be used to implement microcontroller 1808 and Bluetooth transceiver 1810 as will be appreciated by persons skilled in the art.

Microcontroller 1808 is configured to perform operations relating to monitoring and control of pill dispensing by pill dispensing assembly 100, to communicate with a companion application running on a mobile device, and to perform various other operations as will be described herein. Bluetooth transceiver 1810 is configured to enable microcontroller 1810 to wirelessly communicate with the companion application running on the mobile device in accordance with the BLUETOOTH® wireless communication protocol. However, it is to be understood that various other standard or proprietary wireless communication protocols may be utilized to enable such communication.

As further shown in FIG. 18, electronic system 1800 further includes a rechargeable battery 1832, a charger 1830 and a charging port 1818, wherein charging port 1818 comprises part of a user interface 1806 of electronic system 1800. Rechargeable battery 1832 is connected to BLE module 1802 and serves to power BLE module 1802 as well as various other components within electronic system 1802 that are connected thereto. In an embodiment, rechargeable battery 1832 comprises a rechargeable Lithium Polymer (LiPo) Battery, although this is merely one example and any suitable type of rechargeable battery may be used. Charger 1830 (e.g., a LiPo charger) is connected between charging port 1818 and rechargeable battery 1832 and operates to recharge rechargeable battery 1832 when rechargeable battery 1832 is depleted and a suitable power source is connected to charging port 1818. In one embodiment, charging port 1818 comprises a micro USB charging port, although this example is not intended to be limiting and other types of charging ports may be used. Charging port 1818 be analogous to charging port 304 as described above in reference to FIG. 3.

In an embodiment, microcontroller 1808 is configured to enter a reduced-power sleep state after a period of inactivity. For example, microcontroller 1808 may be configured to perform essentially no operations during the sleep state other than counting time. Such functionality advantageously serves to conserve power. To dispense a pill, however, microcontroller 1808 must receive a wake-up signal that will transition microcontroller 1808 to a wake state in which it consumes relatively more power. In an embodiment, such a wake-up signal will be generated when a user presses a push button switch 1822 that comprises part of user interface 1806. For example, in an embodiment, a single press on push button switch 1822 will wake up microcontroller 1808 so that it can perform operations relating to dispensing a pill. Push button switch 1822 may be analogous to multi-purpose button 302 as described above in reference to FIG. 3.

In an embodiment, push button switch 1822 may also be used to initiate a Bluetooth pairing process between microcontroller 1808 and the aforementioned mobile device after microcontroller 1808 has been placed in the wake state. For example, in an embodiment, pressing push button switch 1822 twice in relatively rapid succession will cause such a Bluetooth pairing process to be initiated. Push button switch 1822 may also be used to perform other functions in addition to those noted above. The function that is performed in response to actuation of push button switch 1822 may vary, for example, based on how long push button switch 1822 is pressed or on how many times push button switch 1822 is pressed.

As further shown in FIG. 18, user interface 1806 of electronic system 1800 comprises a light-emitting diode (LED) 1820. Microcontroller 1808 is configured to use LED 1820 to convey information to a user of pill dispensing assembly 100. For example, microcontroller 1808 may cause LED 1820 to generate patterns of light (e.g., steady, blinking, slow blinking, fast blinking, or other patterns) and/or colors of light (in an embodiment in which the LED comprises a multi-color LED) to convey various items of information to the user. In an embodiment, LED 1820 may be used to convey items of information such as, but not limited to: microcontroller 1808 is in a wake state, microcontroller 1808 is in a sleep state, a Bluetooth pairing process has been initiated, a Bluetooth pairing process has completed successfully, a Bluetooth pairing process has failed, rechargeable battery 1832 requires recharging, rechargeable battery 1832 is currently recharging, rechargeable battery 1832 is fully charged, a pill has been dispensed, an error has occurred in the pill dispensing process, tampering with pill dispensing assembly 100 has occurred, a user should interact with the companion application executing on her mobile device, or the like. In an embodiment, LED 1820 may be integrated with a button of push button switch 1822.

As further shown in FIG. 18, electronic system 1800 further includes a pill delivery and detection subsystem 1804, which itself includes a servomotor 1816, an infrared (IR) emitter 1812 and an IR detector 1814. Each of these components is connected to microcontroller 1808 via a corresponding connection to BLE module 1802.

Servomotor 1816 is attached directly or indirectly to rotating arm 610 of dosing mechanism 602. Microcontroller 1808 is configured to control servomotor 1816 to transition rotating arm 610 from a retracted state to an extended state, thereby causing a pill to be dispensed in the manner described above in reference to FIGS. 6 and 7. As will be discussed elsewhere herein, microcontroller 1808 may initiate such a pill dispensing process only in response to an instruction or signal received from a companion application executing on a mobile device and wirelessly received via Bluetooth transceiver 1810. Microcontroller 1808 may also be configured to control servomotor to partially and/or fully rotate rotating arm 610 of dosing mechanism 602 one or more times to disperse pills that may have clustered at a bottom of central chute 612 of dosing mechanism 602 as also described above in reference to FIGS. 6 and 7.

IR emitter 1812 and IR detector 1814 are each situated on either side of an aperture in a PCB that is disposed within housing 114 of base 104. Such PCB may support various other components of electronic system 1800 including but not limited to BLE module 1802. Microcontroller 1808 is configured to turn on IR emitter 1812 as part of initiating the pill dispensing process but before a pill is dispensed. When IR emitter 1812 is turned on, it transmits an IR signal that is received by IR detector 1814. When a pill is dispensed in the manner described above in reference to FIGS. 6 and 7, the pill will pass through the aperture in the PCB, thereby momentarily blocking the transmission of the IR signal from IR emitter 1812 to IR detector 1814. IR detector 1814 will signal microcontroller 1808 when the IR signal has been blocked, thereby alerting microcontroller 1808 that a pill has been dispensed. This dispensing event can be logged by microcontroller 1808 and microcontroller 1808 can transmit information about the dispensing event to the companion application.

If microcontroller 1808 controls rotating arm 610 (via servomotor 1816) to dispense a pill but IR detector 1814 does not subsequently signal microcontroller 1808 that the IR signal has been blocked, then microcontroller 1808 may determine that the attempt to dispense a pill has failed. This may indicate that there are no more pills left to dispense or that the pills have become blocked above the cavity defined by rotating arm 610—a phenomenon that was discussed above in reference to FIGS. 6 and 7. Microcontroller 1808 may be configured to do nothing in such a circumstance except wait for a new command to dispense a pill from the companion application. Alternatively, microcontroller 1808 may be configured to control servomotor to partially and/or fully rotate rotating arm 610 of dosing mechanism 602 one or more times to disperse pills that have may have clustered at a bottom of central chute 612 of dosing mechanism 602 as also described above in reference to FIGS. 6 and 7. Still further, microcontroller 1808 may signal to a user that a dispensing error has occurred, through activation of LED 1820 and/or communication with the companion mobile application.

As further shown in FIG. 18, electronic system 1800 includes a tamper detection switch 1834. Tamper detection switch 1834 is connected to microcontroller 1808 via a corresponding connection to BLE module 1802. Tamper detection switch 1834 may comprise a switch that is disposed at the bottom of circular recess 802 within top portion 120 of housing 114 of base 104. When pill bottle 102 is locked into circular recess 802 in the manner described above, top end 1104 of pill bottle 102 will be in contact with tamper detection switch 1834, thereby actuating it. This actuated state may be signaled to microcontroller 1808, thereby enabling microcontroller 1808 to determine that pill bottle 102 has been installed into its proper position. However, when a user attempts to force pill bottle 102 out of its locked position (e.g., by rocking or prying pill bottle 102 away from base 104), then top end 1104 of pill bottle 102 may move away from tamper detection switch 1834, thereby causing tamper detection switch 1834 to transition to an unactuated state. This unactuated state may also be signaled to microcontroller 1808, thereby enabling microcontroller 1808 to determine that tampering with pill bottle 102 is occurring. Microcontroller 1808 may be configured to perform one or more operations in response to determining that tampering is occurring, including but not limited to logging a tampering event and transmitting information about the tampering event to the companion application. In an embodiment, microcontroller 1808 may be configured to transition from a sleep state to a wake state in response to actuation or un-actuation of tamper detection switch 1834.

Figure 19:
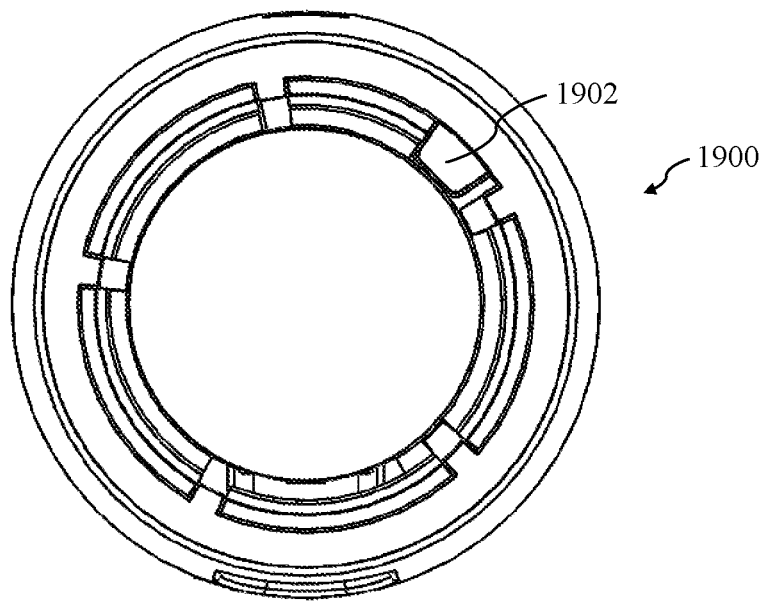
FIG. 19 shows a top view of a base of a pill bottle assembly that includes a tamper detection switch in accordance with an embodiment.
Figure 20:
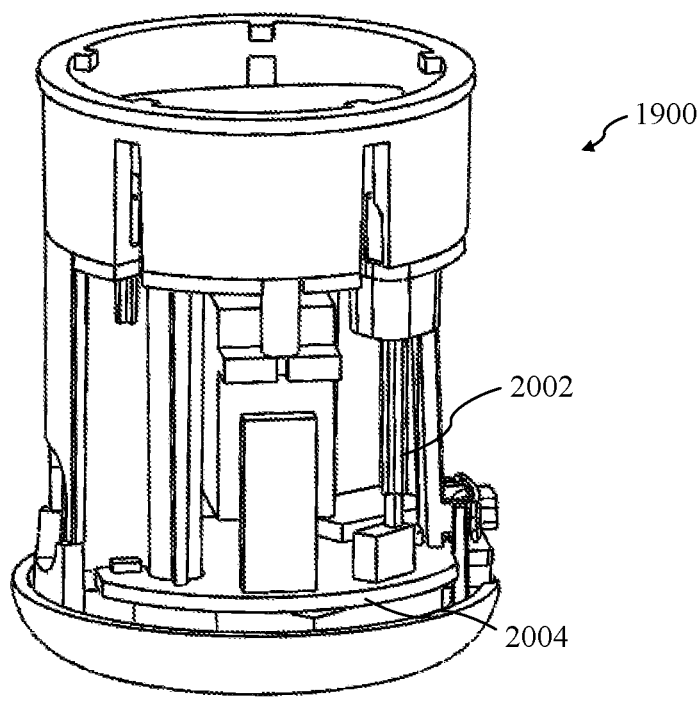
FIG. 20 shows an internal view of a base of the pill bottle assembly of FIG. 18.

To further illustrate the tamper detection feature, FIG. 19 shows a top view of a base 1900 of a pill bottle assembly that includes an example tamper detection switch 1902 (analogous to tamper detection switch 1834 described above in reference to FIG. 18). As shown in FIG. 19, tamper detection switch 1902 is located at the bottom of a circular recess at the top of base 1900 where it will be actuated by the top edge of an installed pill bottle. FIG. 20 shows an internal view of base 1900, which illustrates a connection 2002 between tamper detection switch 1902 and other electronic components on a PCB 2004 disposed within base 1900.

Returning now to the description of FIG. 18, several other components are also connected to microcontroller 1808 via a corresponding connection to BLE module 1802, including an accelerometer 1824 and a near-field communication (NFC) module 1826. Each of these components will now be briefly described.

Accelerometer 1824 may be used to collect information about movement of pill dispensing assembly 100. For example, microcontroller 1808 may collect movement data from accelerometer 1824 while microcontroller 1808 is in a wake state. Such data may be transmitted to the companion application when microcontroller 1808 is communicatively connected thereto. When microcontroller 1808 is not connected to the companion application, then it is possible that such movement-related data may be logged locally with respect to pill dispensing assembly 100 and then later transferred to the companion application after a connection therewith has been established. Such data pertaining to the movement of pill dispensing assembly may be collected over time and analyzed, for example, to detect certain user behaviors (e.g., shaking hands or erratic movements during pill dispensing) that may be indicative of addiction or a predisposition to addiction. Such data may also be analyzed to detect other behaviors or conditions as well.

In an embodiment, microcontroller 1808 may be configured to transition from a sleep to a wake state in response to the detection of movement by accelerometer 1824. In further accordance with such an embodiment, microcontroller 1808 may be configured to transition from the sleep state to a wake state only in response to the detection of movements having an acceleration that exceeds some preprogrammed threshold.

NFC module 1826 may be configured to enable communication between microcontroller 1808 and the mobile device that executes the companion application via well-known NFC protocols. Such NFC communication may be used for example, to cause microcontroller 1808 to wake up and to initiate a BLUETOOTH® pairing process with the mobile device when the mobile device is within a certain proximity to pill dispensing assembly 100.

In another embodiment, electronic system 1800 may also include a temperature sensor (not shown in FIG. 18). Microcontroller 1808 may monitor temperature data produced by the temperature sensor. If microcontroller 1808 determines that the temperature reported by the temperature sensor is too high (e.g., exceeds a threshold), then microcontroller can take certain actions such as shutting down some or all of electronic system 1800. This can help protect electronic system 1800 by avoiding various adverse effects of high heat such as explosion of rechargeable battery 1832.

B. Example Pill Dispensing System

Figure 21:
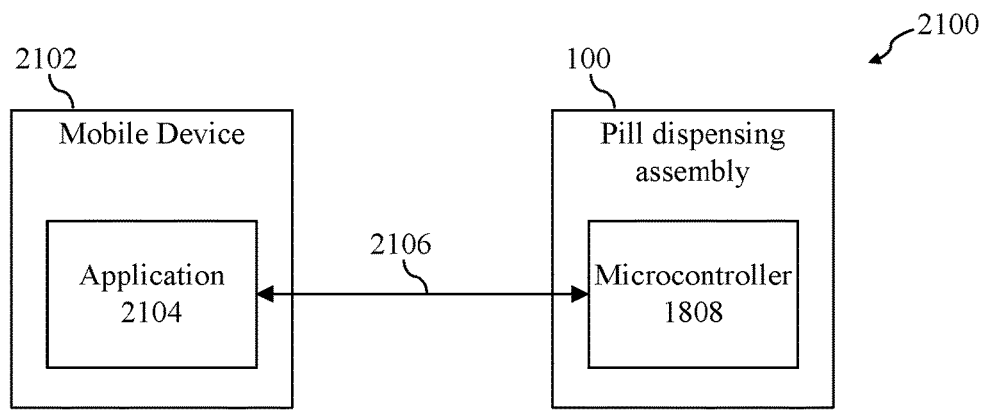
FIG. 21 is a block diagram of a pill dispensing system that includes the pill dispensing assembly of FIG. 1 and an application executing on a mobile device.

Pill dispensing assembly 100 comprises part of a pill dispensing system that also includes an application (also referred to herein as a "companion application") executing on a mobile device (e.g., a smart phone, a tablet computing device, laptop computing device, or the like). This is generally illustrated in FIG. 21, which is a block diagram of a pill dispensing system 2100 that includes pill dispensing assembly 100 and an application 2104 executing on a mobile device 2102. As shown in FIG. 21, in pill dispensing system 2100, application 2104 executing on mobile device 2102 is communicatively connected to microcontroller 1808 of pill dispensing assembly 100 via a wireless communication link 2106, which may comprise, for example, a BLUETOOTH® wireless communication link. Thus, it is to be understood that mobile device 2102 comprises a mobile device 2102 that is configured to support such wireless communication.

Generally speaking, application 2104 is configured to enable a user (e.g., a patient) to dispense pills from pill dispensing assembly 100 and to collect certain information about such dispensing. As will be discussed elsewhere herein, application 2104 may be further configured to provide the information it collects to a remote backend system for storage thereby in a backend database. An example manner of operation of application 2104 will now be described with reference to FIGS. 22-35, which illustrate example graphical user interface (GUI) screens of application 2104. As will be understood to persons skilled in the relevant art(s), application 2104 may cause the GUI screens of FIGS. 22-35 to be rendered to a display of mobile device 2102 upon which application 2104 is executing. In the description that follows, it is to be understood that a reference to a user "activating", "interacting with" or "selecting" a GUI control element encompasses the user employing any of a wide variety of user input mechanisms including but not limited to touching a touch screen, pointing and clicking with a mouse or touchpad, or the like. Moreover, a user may enter data into the GUIs using any of a variety of data entry mechanisms including but not limited to physical keyboard, virtual keyboard, voice control, or the like.

Figures 22, 23:
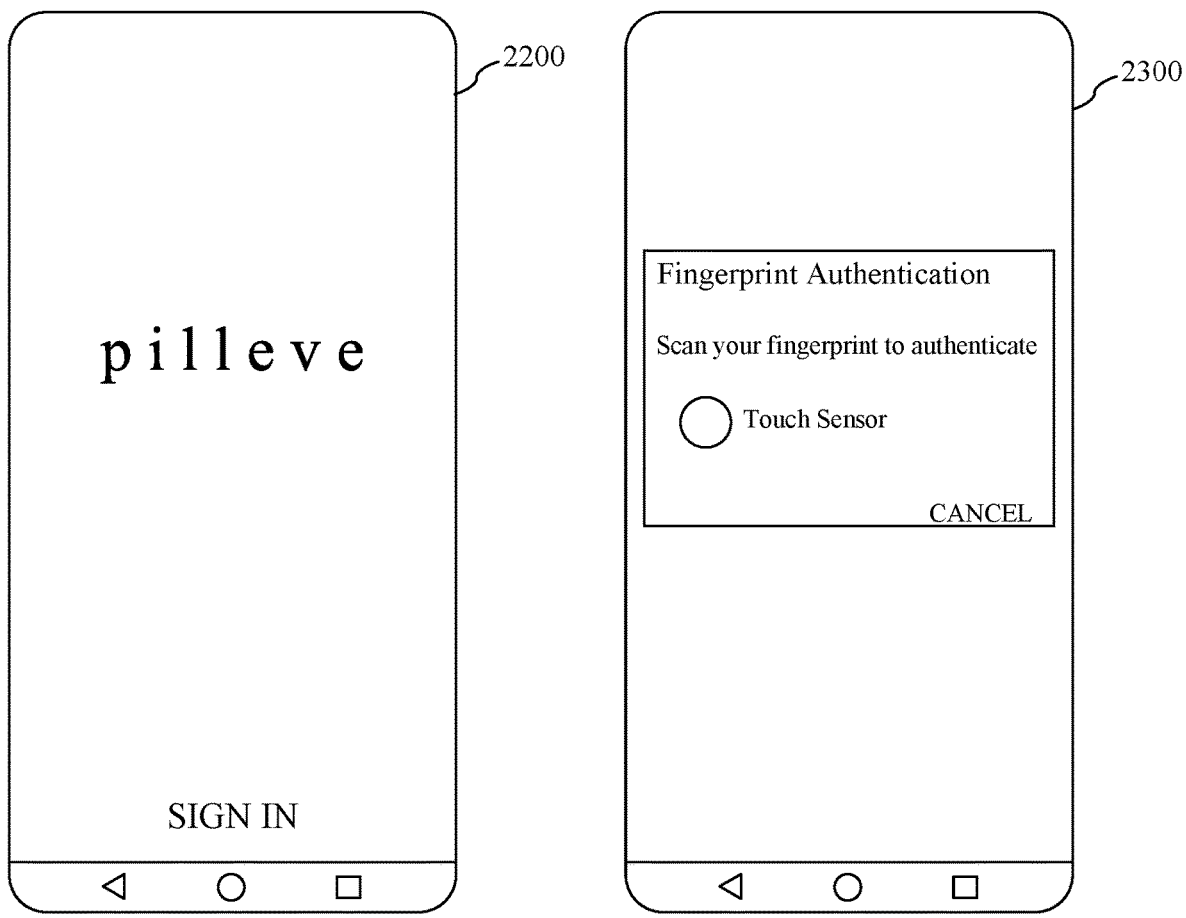

FIG. 22 depicts an example launch GUI screen 2200 of application 2104. As shown in FIG. 22, launch GUI screen 2200 includes an application title ("pilleve") and a user-activatable GUI control element (labelled "SIGN IN"), that a user can activate to initiate a sign-in process of application 2104.

FIG. 23 depicts an example biometric authentication GUI screen 2300 of application 2104. Application 2104 may display biometric authentication GUI screen 2300 after a user has activated the "SIGN IN" GUI control element of launch GUI screen 2200. In embodiments, application 2104 is configured to invoke a biometric authentication process of an operating system (OS) of mobile device 2102 to conduct a biometric check of the user. This biometric check ensures that the user is an authorized user of mobile device 2102 and also enables application 2104 to collect certain identifying items of information about the user (e.g., an email address). As can be seen from FIG. 23, in one embodiment, the biometric authentication mechanism comprises a fingerprint scan which the user carries out by placing a fingertip against a touch sensor of mobile device 2102. However, other types of biometric checking may be used instead or in addition to a fingerprint scan.

FIG. 24 depicts an example sign-in GUI screen 2400 of application 2104. Application 2104 may display sign-in GUI screen 2400 after a user has completed the biometric authentication process described above in reference to FIG. 23. As shown in FIG. 24, sign-in GUI screen 2400 comprises two data entry elements via which a user can input a user name and a passcode, respectively. Such user name and passcode may be used by application 2104 to further authenticate the user. For example, if an invalid user name, invalid passcode, or invalid user name/passcode combination is entered, then application 2104 may deny access to any application features and the user will not be able to advance beyond sign-in GUI screen 2400. Note that in some embodiments, if the user has already successfully signed into application 2104 on mobile device 2102 by providing the required user name and passcode, then sign-in GUI screen 2400 may be bypassed during subsequent launches of application 2104—in such a case, the biometric authentication may be deemed sufficient for user authentication. However, this is only one approach, and in other embodiments both biometric authentication and user-credential-based authentication may be carried out every time application 2104 is launched.

FIG. 25 depicts an informed consent GUI screen 2500 of application 2104. Application 2104 may be configured to display informed consent GUI screen 2500 to first-time users of application 2104 after such users have completed the aforementioned sign-in process. As shown in FIG. 25, informed consent GUI screen 2500 provides the user with information about how user data collected by application 2104 will be used, with whom such data will be shared, and how the privacy of such data will be maintained. Informed consent GUI screen 2500 also includes a user-activatable control element for reading a full document concerning these topics, as well as an "I agree and consent" checkbox control element, via which the user can indicate that she agrees and consents to the relevant provisions. In an embodiment, if the user does not provide the required consent, then application 2104 may deny access to any application features and the user will not be able to advance beyond informed consent GUI screen 2500. If the user does provide her consent, then a record of that may be stored on mobile device 2102 by application 2104 and/or transmitted to a remote device or system (e.g., a remote backend system) for storage thereby (e.g., in a backend database). In certain embodiments, once a user has provided her consent, informed consent GUI screen 2500 may be bypassed during subsequent launches of application 2104.

FIG. 26 depicts an example home GUI screen 2600 of application 2104. Application 2104 may be configured to display home GUI screen 2600 after a user has completed the aforementioned sign-in process and, if necessary, provided her informed consent via informed consent GUI screen 2500. As shown in FIG. 26, home GUI screen 2600 provides information to the user about various application features and how to navigate to them. For example, the user is informed: "To dispense a pill, swipe all the way to the right or use the tabs at the top." Home GUI screen 2600 also provides contact information that may be helpful to user if the user needs application support.

FIG. 27 depicts an example pill dispenser connection GUI screen 2700 of application 2104. Application 2104 may be configured to display pill dispenser connection GUI screen 2700 after a user has indicated that she wishes to dispense a pill but no wireless connection has yet been established between application 2104 and pill dispenser assembly 100. As shown in FIG. 27, pill dispenser connection GUI screen 2700 includes a "SCAN QR CODE" control element. A user can activate this element to initiate a process by which a camera of mobile device 2102 is used to scan a QR code that is associated with pill dispenser assembly 100. For example, the QR code may appear on a label that is affixed to pill dispenser assembly 100. The QR code represents a unique identifier (ID) of pill dispenser assembly 100. In an embodiment, once the unique ID has been captured in this manner, application 2104 will automatically attempt to establish a wireless connection (e.g., a BLUETOOTH® connection) with pill dispensing assembly 100 using the unique ID.

As further illustrated by FIG. 27, instead of using the QR code scanning process, the user may also manually enter the unique ID of pill dispenser assembly 100 into a data entry control element (initially containing the text "Enter Code") of pill dispenser connection GUI screen 2700. The unique ID may also appear on the aforementioned label that is affixed to pill dispenser assembly 100 or made accessible to the user in some other manner Once the unique ID has been provided by the user in this manner, application 2104 will automatically attempt to establish a wireless connection (e.g., a BLUETOOTH® connection) with pill dispensing assembly 100 using the unique ID.

FIG. 28 depicts an example pill dispensing GUI screen 2800 of application 2104. Application 2104 may be configured to display pill dispensing GUI screen 2800 when a user navigates thereto (by swiping, interacting with GUI tabs, or the like). In an alternate embodiment, pill dispensing GUI screen 2800 may be a default home screen of application 2104.

As shown in FIG. 28, pill dispensing GUI screen 2800 includes several GUI control elements via which a user can provide information about any pain that she is experiencing prior to dispensing a pill. For example, a pain level slider is provided via which the user can assign a numeric rating (e.g., on a scale from 0 to 10) to the pain that they are experiencing. In the example embodiment shown in FIG. 28, as the pain level slider is moved to the right, a pain level value displayed on the screen increases from 0 to 10 and a graphic of a face displayed on the screen transitions from a smile, to a frown, and finally to crying. These GUI features provide visual feedback to the user about the level of pain that is represented by the current position of the slider.

Figures 30, 31, 32:
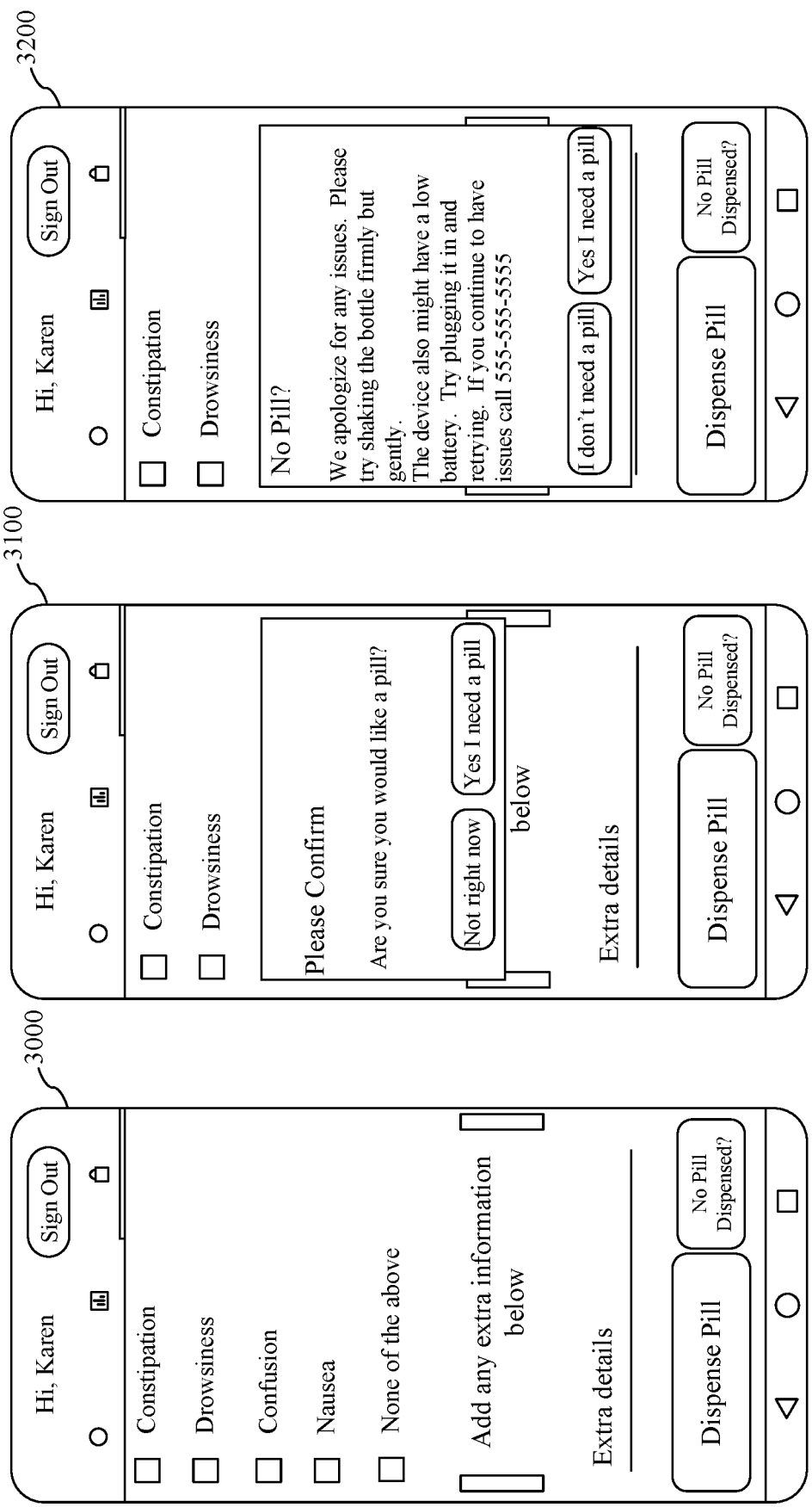

As further shown in FIG. 28, pill dispensing GUI screen 2800 also includes a "Describe your pain" GUI control element. When a user interacts with the "Describe your pain" GUI control element, the element expands to display additional prompts and associated GUI control elements via which the user can provide additional input about their pain. Examples of this are shown in FIGS. 29 and 30, which depict example pill dispensing GUI screens 2900 and 3000, respectively. As shown in FIG. 29, the user may be prompted to provide answers to specific questions about the nature of their pain and how it is has impacted them, and user answers may be provided using radio buttons or other suitable GUI control elements (e.g., check boxes, selectable menu items, or the like). As shown in FIG. 30, the user may also be presented with a data entry element via which the user may simply type in any information about the pain they are experiencing.

In some embodiments, pain information may be provided by the user on a voluntary basis only and need not be provided in order to dispense a pill. In alternate embodiments, the user must provide at least some pain information in order to dispense a pill.

Pill dispensing GUI screen 2800 also includes a "Dispense Pill" GUI control element in the form of a button. In one embodiment, when the user activates this button, a confirmation dialog box is presented via which the user is asked to confirm that they would like to dispense a pill. This dialog box is depicted in example pill dispensing GUI screen 3100 of FIG. 30. In accordance with this embodiment, after the user has confirmed that they would like to dispense a pill, application 2104 sends a signal to microcontroller 1808 of pill dispensing assembly 100 that causes microcontroller 1808 to dispense a pill in the manner previously described.

In an embodiment, when a pill is dispensed, application 2104 sends certain information about the pill dispensing event to a remote backend system (e.g., to one or more remote servers that implement a backend system) for storage thereby (e.g., for storage in a backend database). For example, application 2104 may send information including the unique identifier of pill dispensing assembly 100, a timestamp or other indicator of the date and time when the pill dispensing event occurred, and any pain level or pain description information that may have been input by the user as part of the pill dispensing process. This information also may include an identifier of the user (e.g., the user's email address and/or user name). Accelerometer data collected by pill dispensing assembly 100 and provided to application 2104 (as previously discussed) may also be sent to the remote backend system for storage thereby at this time or at other times depending on how the system is implemented.

Pill dispensing GUI screen 2800 also includes a "No Pill Dispensed?" GUI control element in the form of a button. If the user has requested that a pill be dispensed in the manner described above but pill dispensing assembly 100 has not dispensed a pill, then the user may press this button to obtain options concerning how to proceed. In one embodiment, if the user presses this button, a dialog box is presented that provides the user with guidance concerning how to proceed and contact information for obtaining support. This dialog box is depicted in example pill dispensing GUI screen 3200.

In certain embodiments, microcontroller 1808 of pill dispensing assembly 100 may be capable of automatically determining if an attempt to dispense a pill has failed. For example, as discussed above in reference to FIG. 18, IR detector 1814 may generate signals that enable microcontroller 1808 to determine whether a pill has been dispensed or not. In such embodiments, microcontroller 1808 may be capable of reporting a failed pill dispensing process to application 2104 and application 2104 may present the user with various options based on this information.

FIG. 33 depicts an example statistics GUI screen 3300 of application 2104. Statistics GUI screen 3300 may be accessed by a user to view various items of information tracked by application 2104. This information may be stored locally by application 2104 (e.g., in memory of mobile device 2102) or remotely (e.g., by a remote backend system/ database to which application 2104 may communicatively connect). As shown in FIG. 33, such information may include a total number of pills taken since beginning a prescription, an amount of time that has elapsed since a pill was last taken, a date and time at which a pill was last taken, and a pain level that the user entered the last when a last pill was taken.

FIG. 34 depicts an example chart GUI screen 3400 of application 2104. Chart GUI screen 3400 may be accessed by a user to obtain a graphical representation of how the user's pain levels have varied over time or across pill dispensing events.

FIG. 35 depicts a pain survey GUI screen 3500 of application 2104. Pain survey GUI screen 3500 may be presented to a user as part of the pill dispensing process and/or outside of the pill dispensing process, depending upon the implementation. Pain survey GUI screen 3500 may be used to present a user of application 2104 with an interactive survey or questionnaire via which the user can provide input about their pain symptoms (e.g., location of pain, description of pain, etc.), side effects, and the like. In one embodiment that will be discussed in further detail herein, the data obtained via such survey may be sent in an anonymous manner (e.g., identified by a survey ID only) to a remote pain therapy monitoring service that may generate assessments based on such survey data and those assessments can then be obtained and provided to the user.

Figure 36:
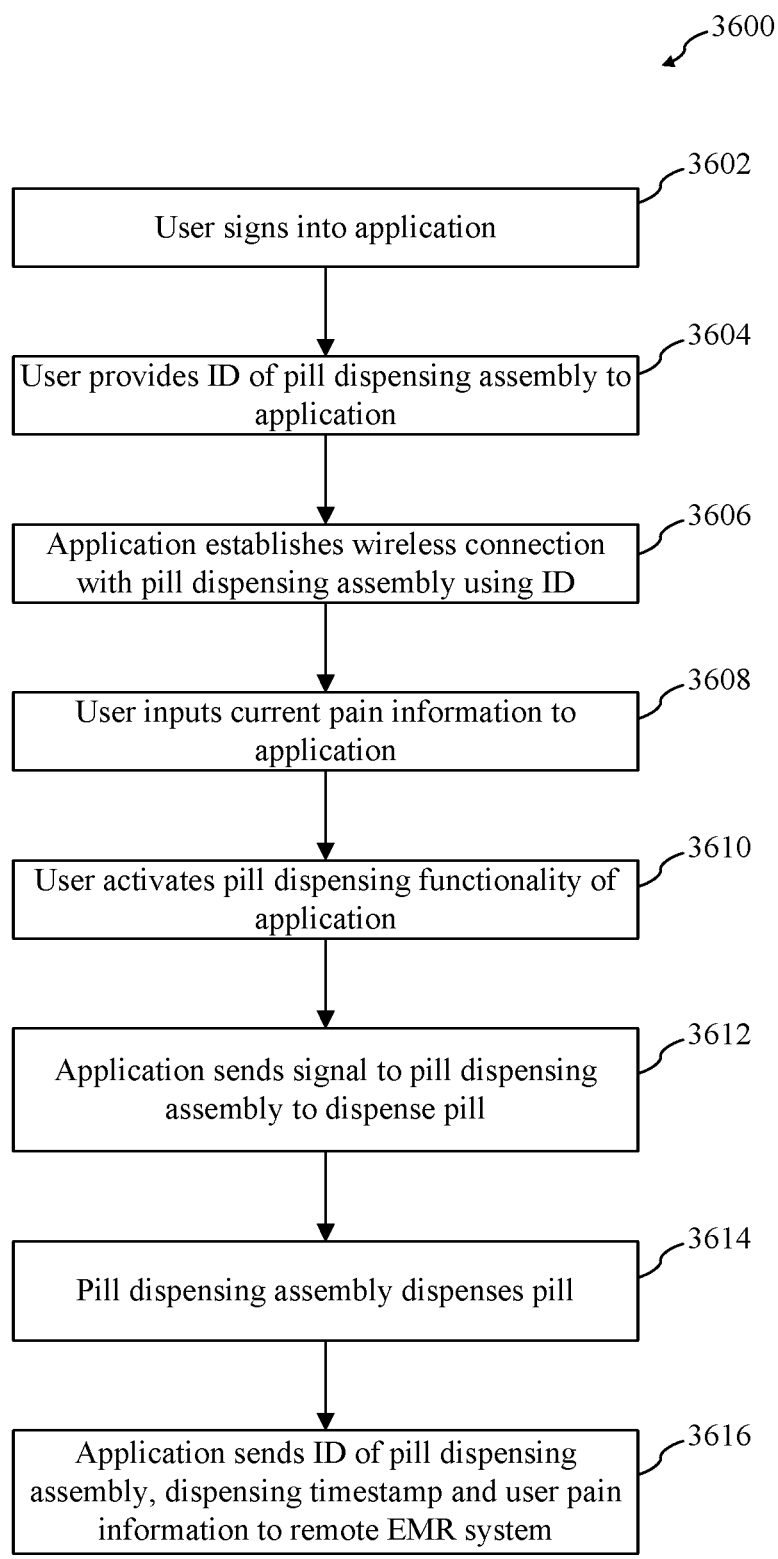
FIG. 36 depicts a flowchart of an example method of use of the application of FIG. 21.

FIG. 36 depicts a flowchart 3600 of an example method of using application 2104 to dispense a pill in accordance with an embodiment. It is to be understood that flowchart 3600 merely represents one method of using application 2104 and that numerous other methods may apply depending on the features of application 2104 and how a user interacts with them.

As shown in FIG. 36, flowchart 3600 begins at step 3602 in which a user signs into application 2104. As noted above, this sign-in process may include biometric authentication of the user (e.g., using a biometric authentication mechanism of mobile device 2102) and/or credential-based authentication of the user (e.g., based on a user-provided user name and passcode). In some embodiments, if the user is a first-time user of application 2104, then after the user has signed into the application in step 3602, the user will be presented by application 3602 with an informed consent request that they must accept to proceed further.

At step 3604, after a successful sign-in, the user provides an identifier (e.g., a unique identifier) of pill dispensing assembly 100 to application 2104. As was previously mentioned, the user may provide this ID by using a QR code scanning feature of application 2104, wherein such QR code scanning feature utilizes a camera of mobile device 2102 to scan a QR code associated with pill dispensing assembly 100. As was also previously mentioned, the user may provide the ID by using a data entry feature of application 2104. Still other methods may be used by which the user may provide the ID to application 2104.

At step 3606, application 2104 establishes a wireless connection with pill dispensing assembly 100 (e.g., with microcontroller 1808 of pill dispensing assembly 100) using the aforementioned ID. In an embodiment, this wireless connection is established using BLUETOOTH® wireless protocols. However, this is only one example, and any of wide variety of wireless communication technologies may be used establish such a wireless connection, including but not limited to IEEE 802.11 (WiFi) and LoRa (Long Range) wireless communication technologies. Such wireless communication may be carried out using radio frequency (RF) communication, infrared communication, or the like. In some embodiments, a wired connection may instead be established using a USB cable or other suitable wired connector.

At step 3608, the user inputs current pain information into application 2104. For example, as discussed above, the user may input a current pain level as well as additional information concerning any pain that they are experiencing. Such information may include survey responses as was previously mentioned. The submission of such current pain information may be optional or required by application 2104 depending upon the implementation.

At step 3610, the user activates the pill dispensing functionality of application 2104. In one previously-described embodiment, this step involves the user activating a GUI control element of application 2104 (e.g., a "Dispense Pill" button), followed by the user confirming their desire to obtain a pill via a subsequently-presented dispense pill confirmation dialog box. However, any number of methods may be used by which the user can indicate to application 2104 that a pill should be dispensed.

At step 3612, responsive to the user activating the pill dispensing functionality of application 2104, application 2104 sends a signal (e.g., a message, command, instruction, code or the like) to pill dispensing assembly 100 (e.g., to microcontroller 1808 of pill dispensing assembly 100) via the previously-established wireless communication link.

At step 3614, response to receiving the signal from application 2104, pill dispensing assembly 100 (e.g., microcontroller 1808 of pill dispensing assembly 100) causes pill to be dispensed. The manner in which pill dispensing assembly 100 operates to dispense a pill has previously been described.

At step 3616, application 2104 sends to a remote backend system certain information that it has collected in relation to the dispensing of the pill for storage thereby. This sending may comprise sending information from mobile device 2102 over a network (e.g., the Internet) to a server within the remote backend system for storage in a backend database. For example, as was previously noted, application 2104 may send the remote backend system information including the ID of pill dispensing assembly 100, a timestamp or other indicator of the date and time when the pill dispensing event occurred, and any pain level or pain description information that may have been input by the user as part of the pill dispensing process. This information also may include an identifier of the user (e.g., the user's email address and/or user name). Accelerometer data collected by pill dispensing assembly 100 and provided to application 2104 (as previously discussed) may also be sent to the remote backend system for storage thereby at this time or at other times depending on how the system is implemented.

Figure 37:
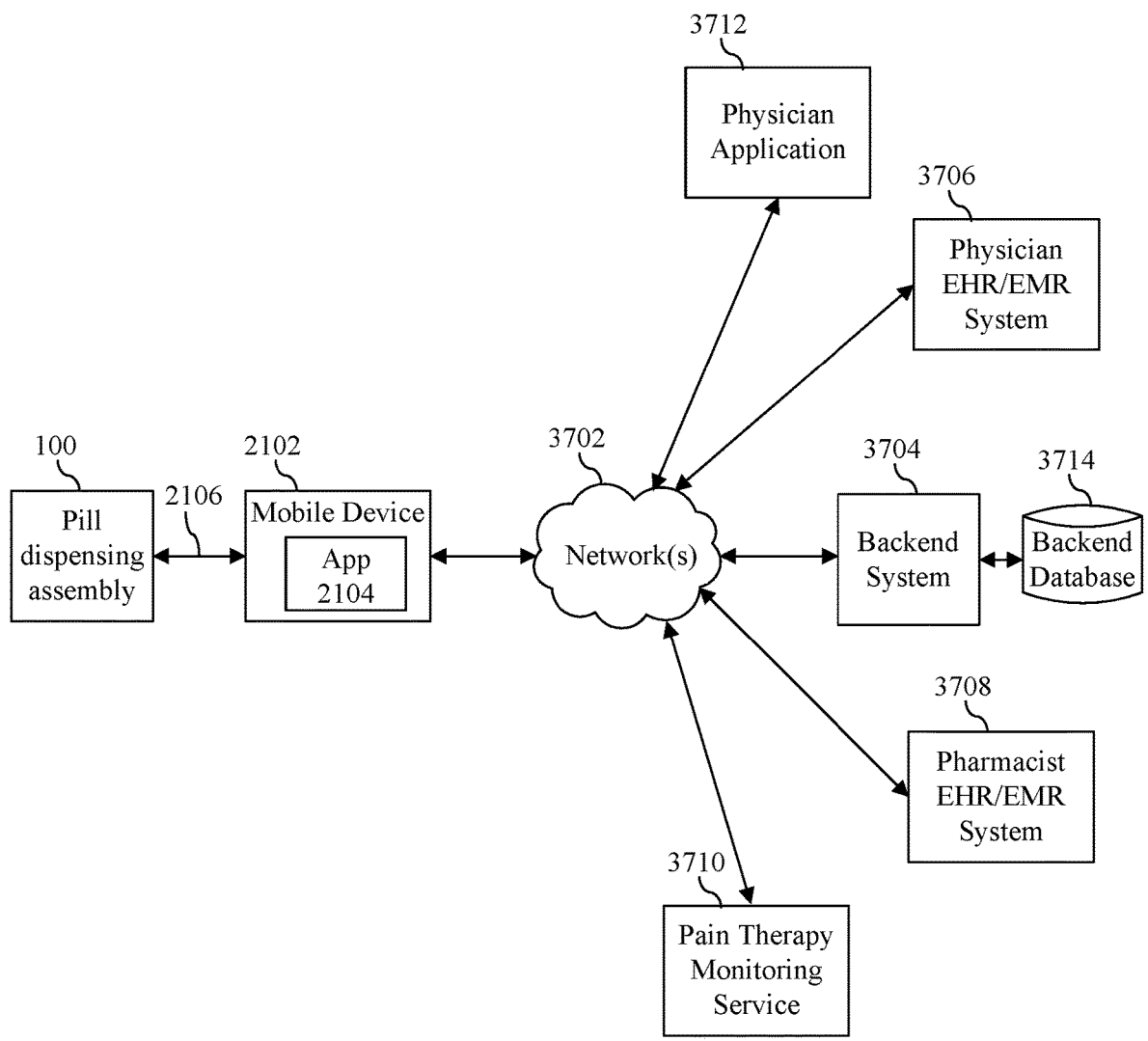
FIG. 37 is a block diagram of a system that include the elements of the pill dispensing system of FIG. 21 as well as backend system/database, a physician electronic health record (EHR)/EMR system, a pharmacist EHR/EMR system, a pain therapy monitoring service, and a physician application.

FIG. 37 is a block diagram that illustrates that pill dispensing assembly 100 and application 2104/mobile device 2102 comprise part of an even larger system 3700 that also includes a backend system 3704, a backend database 3714, a physician EHR/EMR system 3706, a pharmacist EHR/EMR system 3708, a pain therapy monitoring service 3710, and a physician application 3712. Each of these additional components may be connected to application 2104 executing on mobile device 2102 via one or more networks 3702. Network(s) 3702 may comprise one or more networks including but not limited to wide area networks (WANs), local area networks (LANs), enterprise networks, the Internet, etc., and may include one or more of wired and/or wireless portions.

As discussed above, data collected by application 2104 from pill dispensing assembly 100 as well as data obtained from a user of application 2104 (e.g., pain-related input) may be periodically or intermittently transmitted by application 2104 to backend system 3704 for storage thereby in backend database 3714. Backend database 3714 may be stored, for example, in a secure, cloud-based storage system or some other type of storage system/device. In an embodiment, the data stored by backend system 3704 for a particular user may be accessed by that user via her application 2104 (e.g., to obtain statistics, history or charts). Such data may be screened, filtered, summarized, or the like, before being presented to the patient. Backend system 3704 may store the data it receives from application 2104 in a manner that complies with the data privacy provisions of the Health Insurance Portability and Accountability Act (HIPAA). For example, backend system 3704 may de-identify such data to prevent a user's identity from being associated therewith.

Furthermore, application 2104 may be configured to provide the user with a means by which the user can share her data with her physician by allowing the user to upload such data to physician EHR/EMR system 3706. For example, pursuant to a user's request, user data stored in backend database 3714 may be uploaded as a Fast Healthcare Interoperability Resource (FHIR) resource to physician EHR/EMR system 3706 for integration with the user's medical record. In embodiments, this may be accomplished by using an access delegation protocol, such as OAuth 2.0, via which the user can grant limited access to their medical record on physician EHR/EMR system 3706 to application 2104 for the purposes of uploading such data. A similar approach may be used to share such data with a pharmacist EHR/EMR system 3708. Such data may be de-identified, screened, and summarized before being shared with these other systems.

In an embodiment, backend system 3704 may be configured to apply an algorithm to data collected from application 2104 to generate a risk assessment for a patient associated with application 2104. For example, backend system 3704 may apply an algorithm to pill intake data as well as other data collected from application 2104 to generate a risk assessment concerning whether a patient associated with application 2104 is addicted to or likely to become addicted to opioids or other drugs that they have been prescribed, or concerning some other complication. Depending upon the implementation, the algorithm applied by backend system 3704 may comprise a heuristics-based algorithm, an algorithm generated by machine learning or some other form of artificial intelligence. The risk assessment generated by the algorithm may be represented using a text descriptor (e.g., "high risk", "moderate risk", "low risk"), a numeric value or score (e.g., a score between 1 and 10, with 1 being the lowest risk level and 10 being the highest), or in some other suitable manner. Such assessment may be obtained, for example, on behalf of a physician or other caregiver to whom the patient has granted access to such data. The assessment may be delivered to the patient's physician, for example, by uploading it or otherwise transmitting it to physician EHR/EMR system 3706 for presentation to the physician as part of a normal EHR/EMR workflow. However, this is only one example and the risk assessment may be delivered to the physician through other channels as well. Based on the risk assessment, the physician may take appropriate actions on behalf of the patient.

In certain embodiments, the risk assessment may be updated on an ongoing basis by backend system 3704 as more and more data is collected from application 2104. In some embodiments, a risk assessment may be conveyed to a physician or caregiver only if the risk assessment rises to or exceeds a certain predefined risk level.

In certain embodiments, de-identified data being stored in backend database 3714 or data derived therefrom may be utilized in conducting one or more clinical studies relating to drug use, drug misuse, addiction, or other issues. Such de-identified data or data derived therefrom may also be used to identify population trends for government and enforcement officials. For example, by understanding how many pills are being prescribed and where they are being distributed, governmental agencies can more effectively allocate their resources to address drug misuse issues and address unique patient populations that are most at risk using microscopic data. Such de-identified data or data derived therefrom may also be used to identify patient trends for insurance companies, payers and/or healthcare systems. For example, by tapping into such data, larger organizations may be able to understand patient trends and more effectively adapt their operations to efficiently care for different patients. Such data can also be utilized to provide more personalized healthcare options at an institutional level.

As was also discussed above, application 2104 may be configured to accept data about a user's pain, symptoms, etc. as part of an interactive survey. The data obtained via such survey may be sent in an anonymous manner (e.g., identified by a survey ID only) to remote pain therapy monitoring service 3710. Remote pain monitoring service 3710 may generate assessments based on such survey data and then make those assessments available for consumption by the user (e.g., via application 2104 or other means).

As further shown in FIG. 37, system 3700 may comprise a physician application 3712 which may be executing on a computing device connected to network(s) 3702. Physician application 3712 may provide a portal by which a physician can prescribe and alter prescriptions for pain management remotely. In one embodiment, a physician may enter information about a prescription into physician application 3712 and such information may be conveyed both to a pharmacist and to application 2104 for viewing by the patient. Furthermore, any updates made by the physician to the prescription may be immediately provided to the pharmacist and application 2104 for presentation to the patient.

In certain embodiments, application 2104 may be configured to prohibit user access to pills that are stored within pill dispensing assembly 100 under certain conditions. Application 2104 may prohibit access to the pills by not sending the necessary signal to pill dispensing assembly 100 to initiate the pill dispensing mechanism. For example, if a physician provides input to physician application 3712 that the patient should no longer have access to the pills, then physician application 3712 may convey instructions to application 2104 that causes application 2104 to prohibit further access to the pills. Furthermore, application 2104 may automatically shut off access to the pills if it is determined that too many pills have been dispensed within a specified time, if a prescription has changed in a manner that reduces the number of pills that should be taken by the patient, or based on some other automatically-determined conditions.

Although application 2104 is shown executing on mobile device 2102 in FIG. 37, it is to be understood that at least some of the features of application 2104 may be executing on a server that is remotely located with respect to mobile device 2104 and that is connected thereto via network(s) 3702. For example, one or more of the features of application 2104 may be executing on a server within backend system 3704. Such server may comprise a cloud server within a cloud services platform, an enterprise server, or the like.

Also, although the foregoing describes implementations in which the signal for activating the dispensing functionality of pill dispensing assembly 100 emanates from a mobile device that is relatively proximate thereto (e.g., sufficiently proximate for effective BLUETOOTH® communication), it is to be understood that such signal could also emanate from a device that is vastly removed from pill dispensing assembly 100 by using any of a variety of long-range communication protocols including but not limited to those used for cellular telephony and satellite communications.

Furthermore, although only a single pill dispensing assembly 100 and mobile device 2102 with corresponding application 2104 is shown in FIG. 37, it is to be understood that system 3700 may include any number of these components. For example, a very large number (e.g., hundreds of thousands, millions, etc.) of pill dispensing assemblies may be provided to different patients as part of filling their prescriptions and those patients may all install an instance of application 2104 on their mobile devices (or other computing device). Each of those applications may interact with backend system 3704 and the other components of FIG. 37 in a like manner to that described above.

III. Example Mobile Device Implementation

Figure 38:
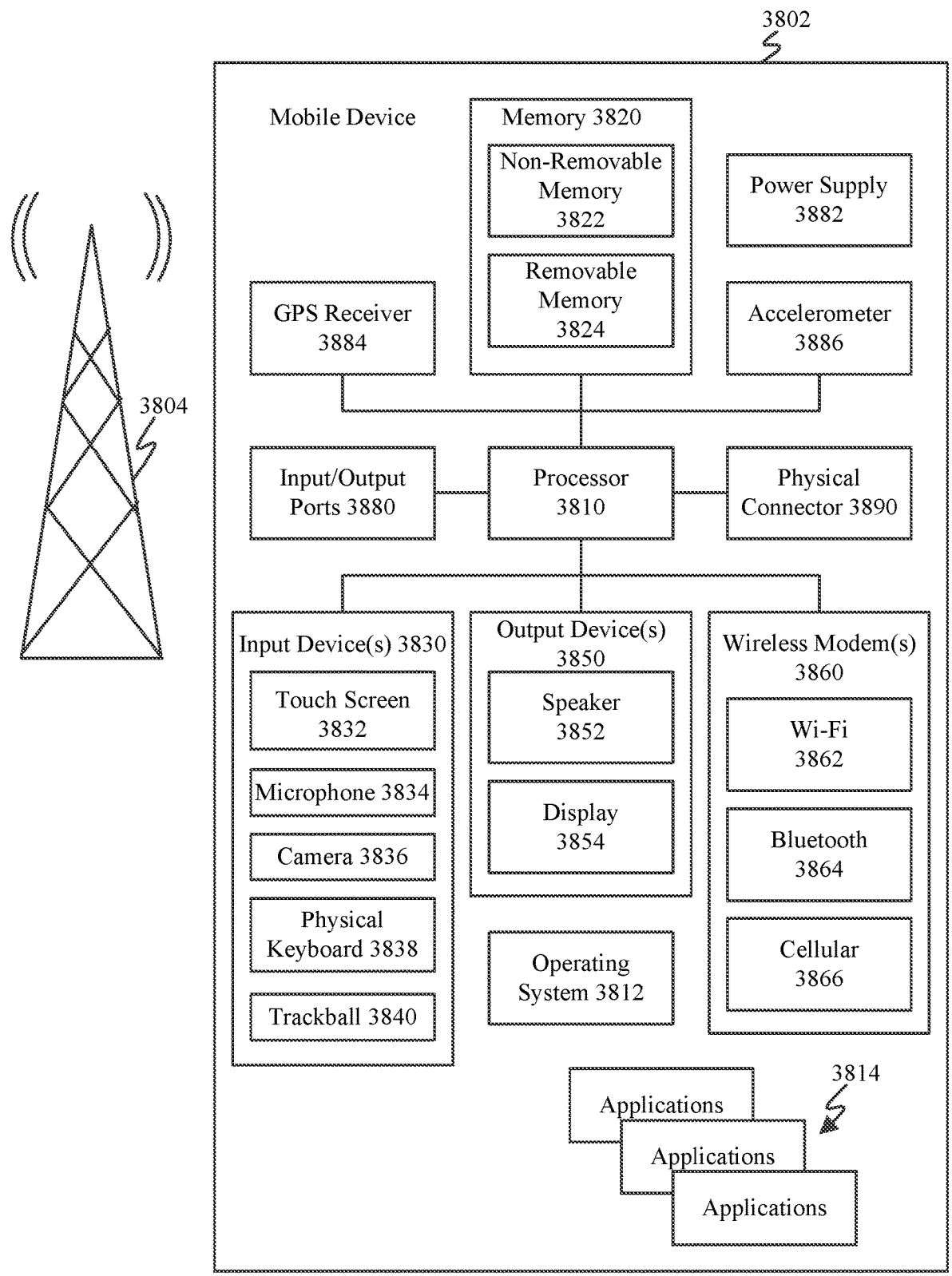
FIG. 38 is a block diagram of an exemplary mobile device that may implement embodiments described herein.

FIG. 38 is a block diagram of an exemplary mobile device 3802 that may implement embodiments described herein.

For example, mobile device 3802 may be used to implement mobile device 2102 of FIG. 20 and/or any of the components respectively described therein. As shown in FIG. 38, mobile device 3802 includes a variety of optional hardware and software components. Any component in mobile device 3802 can communicate with any other component, although not all connections are shown for ease of illustration. Mobile device 3802 can be any of a variety of computing devices (e.g., cell phone, smart phone, handheld computer, Personal Digital Assistant (PDA), etc.) and can allow wireless two-way communications with one or more mobile communications networks 3804, such as a cellular or satellite network, or with a local area or wide area network. Mobile device 3802 can also be any of a variety of wearable computing device (e.g., a smart watch, an augmented reality headset, etc.).

Mobile device 3802 can include a controller or processor 3810 (e.g., signal processor, microprocessor, ASIC, or other control and processing logic circuitry) for performing such tasks as signal coding, data processing, input/output processing, power control, and/or other functions. An operating system 3812 can control the allocation and usage of the components of mobile device 3802 and provide support for one or more application programs 3814 (also referred to as "applications" or "apps"). Application programs 3814 may include common mobile computing applications (e.g., e-mail applications, calendars, contact managers, web browsers, messaging applications) and any other computing applications (e.g., word processing applications, mapping applications, media player applications). Application programs may also include application 2104 as described herein.

Mobile device 3802 can include memory 3820. Memory 3820 can include non-removable memory 3822 and/or removable memory 3824. Non-removable memory 3822 can include RAM, ROM, flash memory, a hard disk, or other well-known memory devices or technologies. Removable memory 3824 can include flash memory or a Subscriber Identity Module (SIM) card, which is well known in GSM communication systems, or other well-known memory devices or technologies, such as "smart cards." Memory 3820 can be used for storing data and/or code for running operating system 3812 and application programs 3814. Example data can include web pages, text, images, sound files, video data, or other data to be sent to and/or received from one or more network servers or other devices via one or more wired or wireless networks. Memory 3820 can be used to store a subscriber identifier, such as an International Mobile Subscriber Identity (IMSI), and an equipment identifier, such as an International Mobile Equipment Identifier (IMEI). Such identifiers can be transmitted to a network server to identify users and equipment.

Mobile device 3802 can support one or more input devices 3830, such as a touch screen 3832, a microphone 3834, a camera 3836, a physical keyboard 3838 and/or a trackball 3840 and one or more output devices 3850, such as a speaker 3852 and a display 3854. Other possible output devices (not shown) can include piezoelectric or other haptic output devices. Some devices can serve more than one input/output function. For example, touch screen 3832 and display 3854 can be combined in a single input/output device. Input devices 3830 can include a Natural User Interface (NUI).

Wireless modem(s) 3860 can be coupled to antenna(s) (not shown) and can support two-way communications between processor 3810 and external devices, as is well understood in the art. Modem(s) 3860 are shown generically and can include a cellular modem 3866 for communicating with the mobile communication network 3804 and/or other radio-based modems (e.g., Bluetooth 3864 and/or Wi-Fi 3862). At least one of wireless modem(s) 3860 is typically configured for communication with one or more cellular networks, such as a GSM network for data and voice communications within a single cellular network, between cellular networks, or between the mobile device and a public switched telephone network (PSTN).

Mobile device 3802 can further include at least one input/output port 3880, a power supply 3882, a satellite navigation system receiver 3884, such as a Global Positioning System (GPS) receiver, an accelerometer 3886, and/or a physical connector 3890, which can be a USB port, IEEE 1394 (FireWire) port, and/or RS-232 port. The illustrated components of mobile device 3802 are not required or all-inclusive, as any components can be deleted, and other components can be added as would be recognized by one skilled in the art.

In an embodiment, mobile device 3802 is configured to implement any of the above-described features of mobile device 2102 or application 2104. Computer program logic for performing the functions of these devices may be stored in memory 3820 and executed by processor 3810.

IV. Example Computer System Implementation

Any of the functions and features of mobile device 2102, application 2104, backend system 3704, physician EHR/EMR system 3706, pharmacist EHR/EMR system 3708, pain therapy monitoring service 3710, physician application 3712, the GUI screens of FIGS. 22-35, and flowchart 3600 of FIG. 36 may be implemented in hardware, or hardware combined with one or both of software and/or firmware, such as being implemented as computer program code/instructions stored in a physical/hardware-based computer readable storage medium and configured to be executed in one or more processors, or being implemented as hardware logic/electrical circuitry (e.g., electrical circuits comprised of transistors, logic gates, operational amplifiers, one or more application specific integrated circuits (ASICs), one or more field programmable gate arrays (FPGAs)). For instance, in an embodiment, one or more functions or features of mobile device 2102, application 2104, backend system 3704, physician EHR/EMR system 3706, pharmacist EHR/EMR system 3708, pain therapy monitoring service 3710, physician application 3712, the GUI screens of FIGS. 22-35, and flowchart 3600 of FIG. 36 may be implemented separately or together in a SoC. The SoC may include an integrated circuit chip that includes one or more of a processor (e.g., a central processing unit (CPU), microcontroller, microprocessor, digital signal processor (DSP), etc.), memory, one or more communication interfaces, and/or further circuits, and may optionally execute received program code and/or include embedded firmware to perform functions. Note that electronic circuits such as ASICs and FPGAs may be used to accelerate various computations such as checksums, hashing, encryption, compression, etc.

Figure 39:
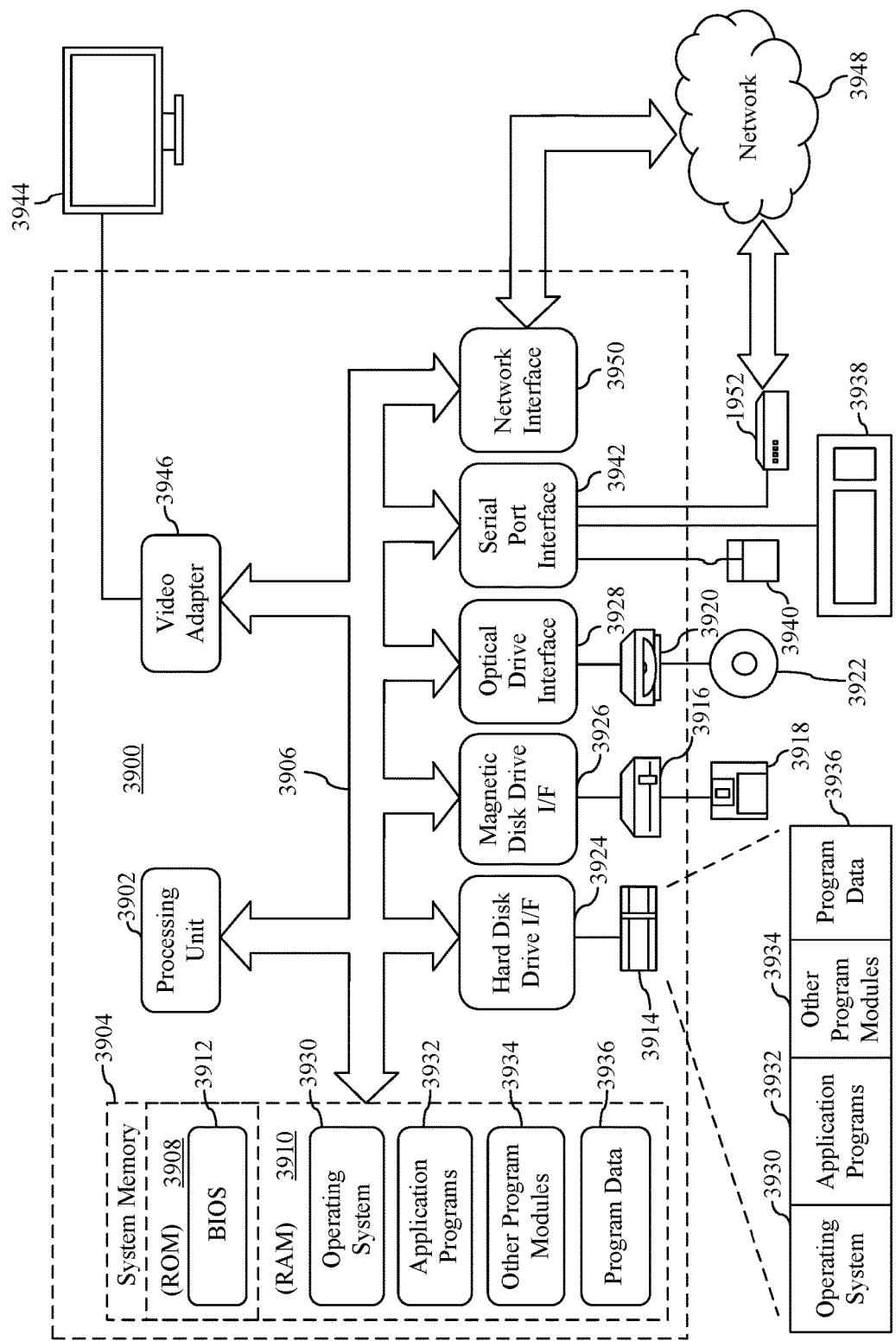
FIG. 39 depicts an example process-based computer system that may be used to implement various embodiments described herein.

FIG. 39 depicts an example processor-based computer system 3900 that may be used to implement various embodiments described herein, including the function and features of mobile device 2102, application 2104, backend system 3704, physician EHR/EMR system 3706, pharmacist EHR/EMR system 3708, pain therapy monitoring service 3710, physician application 3712, the GUI screens of FIGS. 22-35, and flowchart 3600 of FIG. 36 as described above. The description of system 3900 provided herein is provided for purposes of illustration and is not intended to be limiting. Embodiments may be implemented in further types of computer systems, as would be known to persons skilled in the relevant art(s).

As shown in FIG. 39, system 3900 includes a processing unit 3902, a system memory 3904, and a bus 3906 that couples various system components including system memory 3904 to processing unit 3902. Processing unit 3902 may comprise one or more microprocessors or microprocessor cores. Bus 3906 represents one or more of any of several types of bus structures, including a memory bus or memory controller, a peripheral bus, an accelerated graphics port, and a processor or local bus using any of a variety of bus architectures. System memory 3904 includes read only memory (ROM) 3908 and random-access memory (RAM) 3910. A basic input/output system 3912 (BIOS) is stored in ROM 3908.

System 3900 also has one or more of the following drives: a hard disk drive 3914 for reading from and writing to a hard disk, a magnetic disk drive 3916 for reading from or writing to a removable magnetic disk 3918, and an optical disk drive 3920 for reading from or writing to a removable optical disk 3922 such as a CD ROM, DVD ROM, BLU-RAY™ disk or other optical media. Hard disk drive 3914, magnetic disk drive 3916, and optical disk drive 3920 are connected to bus 3906 by a hard disk drive interface 3924, a magnetic disk drive interface 3926, and an optical drive interface 3928, respectively. The drives and their associated computer-readable media provide nonvolatile storage of computer-readable instructions, data structures, program modules and other data for the computer. Although a hard disk, a removable magnetic disk and a removable optical disk are described, other types of computer-readable memory devices and storage structures can be used to store data, such as flash memory cards, digital video disks, random access memories (RAMs), read only memories (ROM), and the like.

A number of program modules or components may be stored on the hard disk, magnetic disk, optical disk, ROM, or RAM. These program modules include an operating system 3930, one or more application programs 3932, other program modules 3934, and program data 3936. In accordance with various embodiments, the program modules may include computer program logic that is executable by processing unit 3902 to perform any or all the functions and features of mobile device 2102, application 2104, backend system 3704, physician EHR/EMR system 3706, pharmacist EHR/EMR system 3708, pain therapy monitoring service 3710, physician application 3712, the GUI screens of FIGS. 22-35, and flowchart 3600 of FIG. 36 as described above.

A user may enter commands and information into system 3900 through input devices such as a keyboard 3938 and a pointing device 3940. Other input devices (not shown) may include a microphone, joystick, game controller, scanner, or the like. In one embodiment, a touch screen is provided in conjunction with a display 3944 to allow a user to provide user input via the application of a touch (as by a finger or stylus for example) to one or more points on the touch screen. These and other input devices are often connected to processing unit 3902 through a serial port interface 3942 that is coupled to bus 3906, but may be connected by other interfaces, such as a parallel port, game port, or a universal serial bus (USB). Such interfaces may be wired or wireless interfaces.

A display 3944 is also connected to bus 3906 via an interface, such as a video adapter 3946. In addition to display 3944, system 3900 may include other peripheral output devices (not shown) such as speakers and printers.

System 3900 is connected to a network 3948 (e.g., a local area network or wide area network such as the Internet) through a network interface or adapter 3950, a modem 3952, or other suitable means for establishing communications over the network. Modem 3952, which may be internal or external, is connected to bus 3906 via serial port interface 3942. As used herein, the terms "computer program medium," "computer-readable medium," and "computer-readable storage medium" are used to generally refer to memory devices or storage structures such as the hard disk associated with hard disk drive 3914, removable magnetic disk 3918, removable optical disk 3922, as well as other memory devices or storage structures such as flash memory cards, digital video disks, random access memories (RAMs), read only memories (ROM), and the like. Such computer-readable storage media are distinguished from and non-overlapping with communication media (do not include communication media). Communication media typically embodies computer-readable instructions, data structures, program modules or other data in a modulated data signal such as a carrier wave. The term "modulated data signal" means a signal that has one or more of its characteristics set or changed in such a manner as to encode information in the signal. By way of example, and not limitation, communication media includes wireless media such as acoustic, RF, infrared and other wireless media. Embodiments are also directed to such communication media.

As noted above, computer programs and modules (including application programs 3932 and other program modules 3934) may be stored on the hard disk, magnetic disk, optical disk, ROM, or RAM. Such computer programs may also be received via network interface 3950, serial port interface 3942, or any other interface type. Such computer programs, when executed or loaded by an application, enable system 3900 to implement features of embodiments of the present methods and systems described herein. Accordingly, such computer programs represent controllers of the system 3900.

Embodiments are also directed to computer program products comprising software stored on any computer useable medium. Such software, when executed in one or more data processing devices, causes a data processing device(s) to operate as described herein. Embodiments of the present methods and systems employ any computer-useable or computer-readable medium, known now or in the future. Examples of computer-readable mediums include but are not limited to memory devices and storage structures such as RAM, hard drives, floppy disks, CD ROMs, DVD ROMs, zip disks, tapes, magnetic storage devices, optical storage devices, MEMs, nanotechnology-based storage devices, and the like.

V. Conclusion

While various embodiments of the present methods and systems have been described above, they have been presented by way of example only, and not limitation. It will be apparent to persons skilled in the relevant art that various changes in form and detail can be made therein without departing from the spirit and scope of the methods and systems. Thus, the breadth and scope of the present methods and systems should not be limited by any of the above-described exemplary embodiments but should be defined only in accordance with the following claims and their equivalents.

What is claimed is:

1. A pill dispensing assembly, comprising:
   a pill bottle comprising a cylindrical body, a closed circular bottom on a bottom end of the cylindrical body, and a circular opening on a top end of the cylindrical body, the cylindrical body and the closed circular bottom defining a pill bottle cavity, the top end of the pill bottle comprising an external radial ridge comprising a plurality of first mating elements;
   a base comprising a housing within which is disposed a dosing mechanism, a top portion of the housing defining a circular recess having an internal edge that surrounds a top portion of the dosing mechanism, the internal edge comprising a plurality of second mating elements that are respectively mated with the plurality of first mating elements to lock the pill bottle to the base, the pill bottle cavity and the recess defining an enclosure in which a plurality of pills can be stored atop the top portion of the dosing mechanism;
   the top portion of the dosing mechanism comprising a ramp and a rotating arm that is rotatable from a retracted state to an extended state, the rotating arm comprising a notch that is located at a bottom of the ramp to accept a pill from among the plurality of pills when the rotating arm is in the retracted state, the rotation of the rotating arm to the extended state bringing the notch and a pill disposed therein to a position in which the pill will drop through an aperture in a bottom portion of the dosing mechanism into a channel that connects the aperture in the bottom portion of the dosing mechanism to a dispensing slot in the housing of the base; and
   a sleeve comprising a circular bottom that includes a plurality of third mating elements that are respectively mated with the plurality of second mating elements, thereby locking the sleeve to the base and also locking the plurality of first mating elements of the pill bottle between the sleeve and the base.

2. The pill dispensing assembly of claim 1, wherein the base further comprises:
   a tamper detection switch disposed at a bottom of the circular recess in the top portion of the housing of the base; and
   a microcontroller connected to the tamper detection switch and configured to detect when the tamper detection switch is an actuated state or an unactuated state;
   wherein the tamper detection switch is placed in the actuated state when the pill bottle is placed into a locked position within the circular recess in the top portion of the housing of the base, and wherein the tamper detection switch is placed in the unactuated state when the pill bottle is moved away from the locked position.

3. The pill dispensing assembly of claim 1, wherein the base further comprises:
   an accelerometer that generates acceleration data when the pill dispensing assembly is moved; and
   a microprocessor that is connected to the accelerometer and is configured to collect the acceleration data therefrom.

4. The pill dispensing assembly of claim 1, wherein the plurality of first mating elements comprises a plurality of bayonet-shaped female snap connectors and the plurality of second mating elements comprises a plurality of rib-shaped male snap connectors that are configured to respectively engage with the plurality of bayonet-shaped female snap connectors via rotation of the pill bottle relative to the base.

5. The pill dispensing assembly of claim 1, wherein the sleeve comprises a surface upon which a prescription label is affixed.

6. The pill dispensing assembly of claim 1, wherein the plurality of first mating elements comprises a plurality of bayonet-shaped female snap connectors, the plurality of second mating elements comprises a plurality of rib-shaped male snap connectors that are configured to respectively engage with the plurality of bayonet-shaped female snap connectors via rotation of the pill bottle relative to the base, and the plurality of third mating elements comprise a plurality of connectors that are configured to respectively engage with hooks that extend from the plurality of rib-shaped male snap connectors.

7. The pill dispensing assembly of claim 6, wherein the sleeve comprises an elongated gap that is configured to guide a removal tool between the sleeve and the base to break the connectors.

8. The pill dispensing assembly of claim 6, wherein the circular bottom of the sleeve further comprises a plurality of lugs that extend downward therefrom into corresponding gaps between the plurality of bayonet-shaped female snap connectors, thereby impeding rotation of the pill bottle relative to either the base or the sleeve.

9. The pill dispensing assembly of claim 1, wherein the base further comprises:
- a servomotor that is attached to the rotating arm;
- a wireless communication interface; and
- a microcontroller that is connected to the servomotor and the wireless communication interface, the microcontroller being configured to receive a signal via the wireless communication interface and, in response to receiving the signal, cause the servomotor to rotate the rotating arm from the retracted state to the extended state, thereby dispensing a pill.

10. The pill dispensing assembly of claim 9, wherein the base further comprises:
- an infrared (IR) emitter and an IR detector disposed on a printed circuit board (PCB) within a cavity in the base, the IR emitter being configured to emit an IR signal to the IR detector across an aperture in the PCB, the aperture in the PCB being part of the channel that connects the aperture in the bottom portion of the dosing mechanism to the dispensing slot, the IR detector being configured to notify the microcontroller when the IR signal has been blocked by passage of a pill through the channel.

11. The pill dispensing assembly of claim 1, wherein the ramp comprises a chute that is positioned above the notch when the rotating arm is in the retracted state, the chute having a relatively steeper incline than a remainder of the ramp.

12. The pill dispensing assembly of claim 11, wherein the chute comprises a protuberance that extends upward therefrom to propel pills that are sliding down the chute away from each other.

13. The pill dispensing assembly of claim 11, wherein the rotating arm comprises one or more elevated ridges that are rotated into an area at a bottom of the chute when the rotating arm is rotated out of the retracted position.

14. The pill dispensing assembly of claim 13, further comprising:
- a servomotor that is attached to the rotating arm; and
- a microcontroller that is connected to the servomotor, the microcontroller being configured to cause the servomotor to partially or fully rotate the rotating arm one or more times in response to determining that dispensing of a pill has been blocked.

15. A pill dispensing assembly, comprising:
- a base comprising a housing within which is disposed a dosing mechanism, a top portion of the housing defining a circular recess having an internal edge that surrounds a top portion of the dosing mechanism, the internal edge comprising a plurality of first mating elements that are configured to be mated respectively with a plurality of second mating elements disposed on an external radial ridge at a top end of a pill bottle to lock the pill bottle to the base, the recess and the pill bottle when locked to the base defining an enclosure in which a plurality of pills can be stored atop the top portion of the dosing mechanism;
- the top portion of the dosing mechanism comprising a ramp and a rotating arm that is rotatable from a retracted state to an extended state, the rotating arm comprising a notch that is located at a bottom of the ramp to accept a pill from among the plurality of pills when the rotating arm is in the retracted state, the rotation of the rotating arm to the extended state bringing the notch and a pill disposed therein to a position in which the pill will drop through an aperture in a bottom portion of the dosing mechanism into a channel that connects the aperture to a dispensing slot in the housing of the base;
- wherein the base further comprises:
  - a servomotor that is attached to the rotating arm;
  - a wireless communication interface; and
  - a microcontroller that is connected to the servomotor and the wireless communication interface, the microcontroller being configured to receive a signal via the wireless communication interface and, in response to receiving the signal, cause the servomotor to rotate the rotating arm from the retracted state to the extended state, thereby dispensing the pill.

16. The pill dispensing assembly of claim 15, wherein the plurality of first mating elements comprises a plurality of rib-shaped male snap connectors and the plurality of second mating elements comprises a plurality of bayonet-shaped female snap connectors that are configured to respectively engage with the rib-shaped male snap connectors via rotation of the pill bottle relative to the base.

17. The pill dispensing assembly of claim 15, further comprising:
- a sleeve comprising a circular bottom that includes a plurality of third mating elements that are configured to respectively mate with the plurality of first mating elements, thereby locking the sleeve to the base and also locking the plurality of second mating elements of the pill bottle between the sleeve and the base.

18. The pill dispensing assembly of claim 17, wherein the plurality of first mating elements comprises a plurality of rib-shaped male snap connectors, the plurality of second mating elements comprises a plurality of bayonet-shaped female snap connectors that are configured to respectively engage with the rib-shaped male snap connectors via rotation of the pill bottle relative to the base, and the plurality of third mating elements comprise a plurality of connectors that are configured to respectively engage with hooks that extend from the plurality of rib-shaped male snap connectors.

19. A pill dispensing assembly, comprising:
- a base comprising a housing within which is disposed a dosing mechanism, a top portion of the housing defining a recess within which a top portion of the dosing mechanism is exposed, the top portion of the housing being adapted to connect to a pill bottle such that the pill bottle forms an enclosure over the recess and the top portion of the dosing mechanism in which a plurality of pills can be stored;

the top portion of the dosing mechanism having a ramp and a rotating arm that is rotatable from a retracted state to an extended state, the rotating arm comprising a notch that is located at a bottom of the ramp to accept a pill from among a plurality of pills stored within the pill bottle when the rotating arm is in the retracted state, the rotation of the rotating arm to the extended state bringing the notch and a pill disposed therein to a position in which the pill will drop through an aperture in a bottom portion of the dosing mechanism into a channel that connects the aperture to a dispensing slot in the housing of the base;

the ramp comprising a chute that is positioned above the notch when the rotating arm is in the retracted state, the chute having a relatively steeper incline than a remainder of the ramp.

20. The pill dispensing assembly of claim 19, wherein the chute comprises a protuberance that extends upward therefrom to propel pills that are sliding down the chute away from each other.

\* \* \* \* \*